United States Patent [19]
Unger

[11] Patent Number: 5,985,246
[45] Date of Patent: Nov. 16, 1999

[54] CONTRAST AGENTS FOR ULTRASONIC IMAGING AND METHODS FOR PREPARING THE SAME

[75] Inventor: Evan C. Unger, Tucson, Ariz.

[73] Assignee: Imarx Pharmaceutical Corp., Tucson, Ariz.

[21] Appl. No.: 08/888,426

[22] Filed: Jul. 8, 1997

Related U.S. Application Data

[62] Division of application No. 08/665,719, Jun. 18, 1996, which is a division of application No. 08/468,056, Jun. 6, 1995, Pat. No. 5,571,497, which is a division of application No. 08/395,683, Feb. 28, 1995, Pat. No. 5,456,901, which is a division of application No. 08/163,039, Dec. 6, 1993, which is a division of application No. 08/085,608, Jun. 30, 1993, Pat. No. 5,334,381, which is a division of application No. 08/018,112, Feb. 17, 1993, abandoned, which is a division of application No. 07/967,974, Oct. 27, 1992, Pat. No. 5,352,435, which is a division of application No. 07/818,069, Jan. 8, 1992, Pat. No. 5,230,882, which is a division of application No. 07/750,877, Aug. 26, 1991, Pat. No. 5,123,414, which is a division of application No. 07/569,828, Aug. 20, 1990, Pat. No. 5,088,499, which is a continuation-in-part of application No. 07/455,707, Dec. 22, 1989, abandoned.

[51] Int. Cl.$^6$ .......................... A61K 49/04; A61K 9/127; B01J 13/02; B32B 5/16
[52] U.S. Cl. .................. 424/9.51; 424/9.52; 424/450; 264/4; 427/213.3; 428/402.2
[58] Field of Search .................. 424/9.52, 9.51, 424/450; 427/2.14, 213.3; 428/402.2; 264/4, 4.1; 600/458, 441

[56] References Cited

U.S. PATENT DOCUMENTS

| | | | |
|---|---|---|---|
| 3,015,128 | 1/1962 | Sommerville et al. | 18/2.6 |
| 3,291,843 | 12/1966 | Fritz et al. | 260/614 |
| 3,293,114 | 12/1966 | Kenaga et al. | 162/168 |
| 3,479,811 | 11/1969 | Walters | 57/153 |
| 3,488,714 | 1/1970 | Walters et al. | 161/161 |
| 3,532,500 | 10/1970 | Priest et al. | 96/91 |
| 3,557,294 | 1/1971 | Dear et al. | 424/342 |
| 3,594,326 | 7/1971 | Himmel et al. | 252/316 |
| 3,615,972 | 10/1971 | Morehouse et al. | 156/79 |
| 3,650,831 | 3/1972 | Jungermann et al. | 134/27 |
| 3,732,172 | 5/1973 | Herbig et al. | 252/316 |
| 3,873,564 | 3/1975 | Schneider et al. | 260/309.6 |
| 3,945,956 | 3/1976 | Garner | 260/2.5 B |

(List continued on next page.)

FOREIGN PATENT DOCUMENTS

| | | |
|---|---|---|
| 641363 | 3/1990 | Australia . |
| B-30351/89 | 3/1993 | Australia . |
| 0 052 575 | 5/1982 | European Pat. Off. . |
| 0 107 559 | 5/1984 | European Pat. Off. . |
| 0 077 752 B1 | 3/1986 | European Pat. Off. . |
| 0 243 947 | 4/1987 | European Pat. Off. . |
| 0 231 091 | 8/1987 | European Pat. Off. . |
| 0 272 091 | 6/1988 | European Pat. Off. . |
| 0 320 433 A2 | 12/1988 | European Pat. Off. . |
| 0 324 938 | 7/1989 | European Pat. Off. . |
| 0 338 971 | 10/1989 | European Pat. Off. . |
| 357163 A1 | 3/1990 | European Pat. Off. . |
| 0 361 894 | 4/1990 | European Pat. Off. . |
| 0 216 730 | 1/1991 | European Pat. Off. . |
| 0 467 031 A2 | 5/1991 | European Pat. Off. . |
| 0 357 164 B1 | 10/1991 | European Pat. Off. . |
| 0 458 745 A1 | 11/1991 | European Pat. Off. . |
| 441468 A2 | 8/1992 | European Pat. Off. . |
| 0 314 764 B1 | 9/1992 | European Pat. Off. . |
| 0 554 213 A1 | 8/1993 | European Pat. Off. . |
| 0 586 875 | 3/1994 | European Pat. Off. . |
| 0 614 656 A1 | 9/1994 | European Pat. Off. . |
| 0 727 225 A2 | 8/1996 | European Pat. Off. . |

(List continued on next page.)

OTHER PUBLICATIONS

Desir et al., "Assessment of regional myocardial perfusion with myocardial contrast echocardiography in a canine model of varying degrees of coronary stenosis", *Am. Heart J.,* Jan., 1994, 127(1), 56–63.

Sekins et al., "Lung Cancer Hyperthermia via Ultrasound and PFC Liquids", *Published in Proceedings of 5th International Symposium on Hyperthermic Oncology,* Kyoto, Japan, Aug. 29–Sep. 3, 1998, 3 pages.

Pietersen, "A New Warning System for Fires of Electrical Origin", *CERN European Organization for Nuclear Research, Health and Safety Division,* Mar., 1977, 1–5.

Villanueva et al., "Characterization of Spatial Patters of Flow Within the Reperfused Myocardium by Myocardial Contrast Echocardiography", *Circulation,* vol. 88, No. 6, pp. 2596–2606 (Dec. 1993).

Feinstein, Steven B., "Myocardial Perfusion Imaging: Contrast Echocardiography Today and Tomorrow," *Journal of the American College of Cardiology,* 8(1):251–253 (1986).

Keller et al., "The Behavior of Sonicated Albumin Microbubbles Within the Microcirulation: A Basis for Their Use During Myocardial Contrast Echocardiography", *Circulation Res.,* 65(2): 458–465 (1989).

Lincoff et al., "Perfluoro–n–butane: A Gas for Maximum Duration Retinal Tamponade," *Arch Ophthalmology,* 101:460–462 (1983).

Remington's Pharmaceutical Sciences, John Hoover, managing ed., Mack Publishing Company, Easton, PA, pp. 295–298; 736; 1242–1244 (1975).

*Handbook of Pharmaceutical Excipients,* American Pharmaceutical Association, Washington, D.C. and The Pharmaceutical Society of Great Britain, London, England, pp. 181–183 (1986).

(List continued on next page.)

*Primary Examiner*—Jose' G. Dees
*Assistant Examiner*—Michael G. Hartley
*Attorney, Agent, or Firm*—Woodcock Washburn Kurtz Mackiewicz & Norris LLP

[57] ABSTRACT

Liposomes suitable as ultrasound contrast agents which contain media of various types including gases, gaseous precursors activated by pH, temperature or pressure, as well as other solid or liquid contrast enhancing agents, are described. Methods of using the same as ultrasound contrast agents are also disclosed. The present invention also comprises novel methods for synthesizing liposomes having encapsulated therein gases.

69 Claims, 6 Drawing Sheets

U.S. PATENT DOCUMENTS

| | | | |
|---|---|---|---|
| 3,960,583 | 6/1976 | Netting et al. | 106/122 |
| 3,968,203 | 7/1976 | Spitzer et al. | 424/47 |
| 4,027,007 | 5/1977 | Messina | 424/46 |
| 4,089,801 | 5/1978 | Schneider | 252/316 |
| 4,108,806 | 8/1978 | Cohrs et al. | 521/54 |
| 4,138,383 | 2/1979 | Rembaum et al. | 260/29.7 H |
| 4,162,282 | 7/1979 | Fulwyler et al. | 264/9 |
| 4,179,546 | 12/1979 | Garner et al. | 521/56 |
| 4,192,859 | 3/1980 | Mackaness et al. | 424/5 |
| 4,224,179 | 9/1980 | Schneider | 252/316 |
| 4,229,360 | 10/1980 | Schneider et al. | 260/403 |
| 4,265,251 | 5/1981 | Tickner | 128/660 |
| 4,276,885 | 7/1981 | Tickner et al. | 128/660 |
| 4,310,505 | 1/1982 | Baldeschwieler et al. | 424/1 |
| 4,310,506 | 1/1982 | Baldeschwieler et al. | 424/1 |
| 4,315,514 | 2/1982 | Drewes et al. | 128/653 |
| 4,331,654 | 5/1982 | Morris | 424/38 |
| 4,342,826 | 8/1982 | Cole | 435/7 |
| 4,344,929 | 8/1982 | Bonsen et al. | 424/15 |
| 4,420,442 | 12/1983 | Sands | 264/13 |
| 4,421,562 | 12/1983 | Sands et al. | 106/75 |
| 4,426,330 | 1/1984 | Sears | 260/403 |
| 4,427,649 | 1/1984 | Dingle et al. | 424/38 |
| 4,428,924 | 1/1984 | Millington | 424/4 |
| 4,442,843 | 4/1984 | Rasor et al. | 128/660 |
| 4,466,442 | 8/1984 | Hilmann et al. | 128/653 |
| 4,533,254 | 8/1985 | Cook et al. | 366/176 |
| 4,534,899 | 8/1985 | Sears | 260/403 |
| 4,540,629 | 9/1985 | Sands et al. | 428/402 |
| 4,544,545 | 10/1985 | Ryan et al. | 424/1.1 |
| 4,549,892 | 10/1985 | Baker et al. | 65/21.4 |
| 4,569,836 | 2/1986 | Gordon . | |
| 4,572,203 | 2/1986 | Feinstein | 128/661 |
| 4,586,512 | 5/1986 | Do-huu et al. | 128/660 |
| 4,603,044 | 7/1986 | Geho et al. | 424/9 |
| 4,615,879 | 10/1986 | Runge et al. | 424/9 |
| 4,620,546 | 11/1986 | Aida et al. | 128/660 |
| 4,646,756 | 3/1987 | Watmough et al. | 128/804 |
| 4,657,756 | 4/1987 | Rasor et al. | 424/9 |
| 4,658,828 | 4/1987 | Dory | 128/660 |
| 4,663,161 | 5/1987 | Mannino et al. | 424/89 |
| 4,675,310 | 6/1987 | Chapman et al. | 514/6 |
| 4,681,119 | 7/1987 | Rasor et al. | 128/660 |
| 4,684,479 | 8/1987 | D'Arrigo | 252/307 |
| 4,689,986 | 9/1987 | Carson et al. | 73/19 |
| 4,693,999 | 9/1987 | Axelsson et al. | 514/174 |
| 4,718,433 | 1/1988 | Feinstein | 128/660 |
| 4,728,575 | 3/1988 | Gamble et al. | 428/402.2 |
| 4,728,578 | 3/1988 | Higgins et al. | 428/462 |
| 4,731,239 | 3/1988 | Gordon | 424/9 |
| 4,737,323 | 4/1988 | Martin et al. | 264/4.3 |
| 4,774,958 | 10/1988 | Feinstein | 128/660.01 |
| 4,775,522 | 10/1988 | Clark, Jr. | 424/9 |
| 4,776,991 | 10/1988 | Farmer et al. | 264/4.3 |
| 4,781,871 | 11/1988 | West, III et al. | 264/4.3 |
| 4,789,501 | 12/1988 | Day et al. | 252/645 |
| 4,790,891 | 12/1988 | Halliday et al. | 149/2 |
| 4,822,534 | 4/1989 | Lencki et al. | 264/4.3 |
| 4,830,858 | 5/1989 | Payne et al. | 424/450 |
| 4,834,964 | 5/1989 | Rosen | 424/9 |
| 4,844,882 | 7/1989 | Widder et al. | 424/9 |
| 4,863,717 | 9/1989 | Keana | 424/9 |
| 4,865,836 | 9/1989 | Long, Jr. | 424/5 |
| 4,877,561 | 10/1989 | Iga et al. | 264/4.3 |
| 4,893,624 | 1/1990 | Lele | 128/399 |
| 4,895,719 | 1/1990 | Radhakrishnan | 424/45 |
| 4,898,734 | 2/1990 | Mathiowitz et al. | 424/426 |
| 4,900,540 | 2/1990 | Ryan et al. | 424/9 |
| 4,918,065 | 4/1990 | Stindl et al. | 514/179 |
| 4,919,895 | 4/1990 | Heldebrant et al. | 422/129 |
| 4,921,706 | 5/1990 | Roberts et al. | 424/450 |
| 4,927,623 | 5/1990 | Long, Jr. | 424/5 |
| 4,933,121 | 6/1990 | Law et al. | 264/4.3 |
| 4,938,947 | 7/1990 | Nicolau et al. | 424/1.1 |
| 4,957,656 | 9/1990 | Cerny et al. | 252/311 |
| 4,981,692 | 1/1991 | Popescu et al. | 424/422 |
| 4,984,573 | 1/1991 | Leunbach | 128/653 |
| 4,985,550 | 1/1991 | Charpiot et al. | 536/18.4 |
| 4,987,154 | 1/1991 | Long, Jr. | 514/772 |
| 4,993,415 | 2/1991 | Long | 128/653 A |
| 4,996,041 | 2/1991 | Arai et al. | 424/9 |
| 5,000,960 | 3/1991 | Wallach | 424/450 |
| 5,004,611 | 4/1991 | Leigh | 424/450 |
| 5,008,050 | 4/1991 | Cullis et al. | 264/4.3 |
| 5,008,109 | 4/1991 | Tin | 424/422 |
| 5,013,556 | 5/1991 | Woodle et al. | 424/450 |
| 5,019,370 | 5/1991 | Jay et al. | 424/4 |
| 5,045,304 | 9/1991 | Schneider et al. | 424/9 |
| 5,049,388 | 9/1991 | Knight et al. | 424/450 |
| 5,078,994 | 1/1992 | Nair et al. | 424/501 |
| 5,088,499 | 2/1992 | Unger | 128/662.2 |
| 5,107,842 | 4/1992 | Levene et al. | 128/662.02 |
| 5,114,703 | 5/1992 | Wolf et al. | 424/5 |
| 5,123,414 | 6/1992 | Unger | 128/654 |
| 5,135,000 | 8/1992 | Akselrod et al. | 128/662.02 |
| 5,137,928 | 8/1992 | Erbel et al. | 521/56 |
| 5,141,738 | 8/1992 | Rasor et al. | 424/2 |
| 5,147,631 | 9/1992 | Glajch et al. | 424/9 |
| 5,149,319 | 9/1992 | Unger | 604/22 |
| 5,171,755 | 12/1992 | Kaufman | 514/759 |
| 5,186,922 | 2/1993 | Shell et al. | 128/654 |
| 5,190,982 | 3/1993 | Erbel et al. | 521/56 |
| 5,192,549 | 3/1993 | Barenolz et al. | 424/450 |
| 5,194,266 | 3/1993 | Abra et al. | 424/450 |
| 5,195,520 | 3/1993 | Schlief et al. | 128/660.02 |
| 5,196,183 | 3/1993 | Yudelson et al. | 424/9 |
| 5,196,348 | 3/1993 | Schweighardt et al. | 436/173 |
| 5,198,225 | 3/1993 | Meybeck et al. | 424/450 |
| 5,205,287 | 4/1993 | Erbel et al. | 128/632 |
| 5,205,290 | 4/1993 | Unger | 128/653.4 |
| 5,209,720 | 5/1993 | Unger | 604/22 |
| 5,213,804 | 5/1993 | Martin et al. | 424/450 |
| 5,215,680 | 6/1993 | D'Arrigo | 252/307 |
| 5,219,538 | 6/1993 | Henderson et al. | 428/402.2 |
| 5,228,446 | 7/1993 | Unger et al. | 128/662.02 |
| 5,230,882 | 7/1993 | Unger | 424/9 |
| 5,247,935 | 9/1993 | Cline et al. | 128/653.2 |
| 5,271,928 | 12/1993 | Schneider et al. | 424/9 |
| 5,281,408 | 1/1994 | Unger | 424/4 |
| 5,305,757 | 4/1994 | Unger et al. | 128/662.02 |
| 5,310,540 | 5/1994 | Giddey et al. | 424/9 |
| 5,315,997 | 5/1994 | Widder et al. | 128/653.3 |
| 5,315,998 | 5/1994 | Tachibana et al. | 128/660.01 |
| 5,316,771 | 5/1994 | Barenholz et al. | 424/450 |
| 5,334,381 | 8/1994 | Unger | 424/9 |
| 5,339,814 | 8/1994 | Lasker | 128/653.4 |
| 5,344,930 | 9/1994 | Riess et al. | 544/84 |
| 5,350,571 | 9/1994 | Kaufman et al. | 424/9 |
| 5,352,435 | 10/1994 | Unger | 424/9 |
| 5,354,549 | 10/1994 | Klaveness et al. | 424/3 |
| 5,358,702 | 10/1994 | Unger | 424/9 |
| 5,362,477 | 11/1994 | Moore et al. | 424/9 |
| 5,362,478 | 11/1994 | Desai et al. | 424/9 |
| 5,380,519 | 1/1995 | Schneider et al. | 424/9 |
| 5,393,524 | 2/1995 | Quay | 424/9 |
| 5,409,688 | 4/1995 | Quay | 424/9 |
| 5,410,516 | 4/1995 | Uhlendorf et al. | 367/7 |
| 5,413,774 | 5/1995 | Schneider et al. | 424/9.51 |
| 5,425,366 | 6/1995 | Reinhardt et al. | 128/662.02 |
| 5,433,204 | 7/1995 | Olson | 128/661.08 |
| 5,445,813 | 8/1995 | Schneider et al. | 424/9.51 |
| 5,456,900 | 10/1995 | Unger | 424/9.4 |

| | | | |
|---|---|---|---|
| 5,469,854 | 11/1995 | Unger et al. | 128/662.02 |
| 5,470,582 | 11/1995 | Supersaxo et al. | 424/489 |
| 5,485,839 | 1/1996 | Aida et al. | 128/653.1 |
| 5,487,390 | 1/1996 | Cohen et al. | 128/662.02 |
| 5,496,535 | 3/1996 | Kirkland | 424/9.37 |
| 5,498,421 | 3/1996 | Grinstaff et al. | 424/450 |
| 5,501,863 | 3/1996 | Rössling et al. | 424/489 |
| 5,502,094 | 3/1996 | Moore et al. | 524/145 |
| 5,505,932 | 4/1996 | Grinstaff et al. | 424/9.3 |
| 5,527,521 | 6/1996 | Unger | 424/93 |
| 5,529,766 | 6/1996 | Klaveness et al. | 424/9.52 |
| 5,531,980 | 7/1996 | Schneider et al. | 424/9.52 |
| 5,536,489 | 7/1996 | Lohrmann et al. | 424/9.52 |
| 5,536,490 | 7/1996 | Klaveness et al. | 424/9.52 |
| 5,540,909 | 7/1996 | Schutt | 424/9.52 |
| 5,542,935 | 8/1996 | Unger et al. | 604/190 |
| 5,545,396 | 8/1996 | Albert et al. | 424/93 |
| 5,547,656 | 8/1996 | Unger | 424/9.4 |
| 5,552,133 | 9/1996 | Lambert et al. | 424/9.52 |
| 5,552,155 | 9/1996 | Bailey et al. | 424/450 |
| 5,556,610 | 9/1996 | Yan et al. | 424/9.52 |
| 5,558,092 | 9/1996 | Unger et al. | 128/660.03 |
| 5,558,094 | 9/1996 | Quay | 128/662.02 |
| 5,558,853 | 9/1996 | Quay | 424/9.5 |
| 5,558,854 | 9/1996 | Quay | 424/9.52 |
| 5,558,855 | 9/1996 | Quay | 424/9.5 |
| 5,558,856 | 9/1996 | Klaveness et al. | 424/9.37 |
| 5,560,364 | 10/1996 | Porter | 128/662.02 |
| 5,562,893 | 10/1996 | Lohrmann | 424/9.52 |
| 5,567,413 | 10/1996 | Klaveness et al. | 424/9.51 |
| 5,567,414 | 10/1996 | Schneider et al. | 424/9.52 |
| 5,567,765 | 10/1996 | Moore et al. | 524/801 |
| 5,569,448 | 10/1996 | Wong et al. | 424/9.45 |
| 5,569,449 | 10/1996 | Klaveness et al. | 424/9.51 |
| 5,573,751 | 11/1996 | Quay | 424/9.52 |
| 5,578,292 | 11/1996 | Schneider et al. | 424/9.51 |
| 5,585,112 | 12/1996 | Unger et al. | 424/450 |
| 5,593,680 | 1/1997 | Bara et al. | 424/401 |
| 5,595,723 | 1/1997 | Quay | 424/9.5 |
| 5,605,673 | 2/1997 | Schutt et al. | 424/9.51 |
| 5,606,973 | 3/1997 | Lambert et al. | 128/662.02 |
| 5,614,169 | 3/1997 | Klaveness et al. | 424/9.52 |
| 5,620,689 | 4/1997 | Allen et al. | 424/178.1 |
| 5,626,833 | 5/1997 | Schutt et al. | 424/9.52 |
| 5,639,443 | 6/1997 | Schutt et al. | 424/9.52 |
| 5,643,553 | 7/1997 | Schneider et al. | 424/9.52 |
| 5,672,585 | 9/1997 | Pierschbacher et al. | 514/11 |
| 5,676,928 | 10/1997 | Klaveness et al. | 424/9.32 |
| 5,679,459 | 10/1997 | Riess et al. | 428/402.2 |
| 5,686,060 | 11/1997 | Schneider et al. | 424/9.52 |
| 5,686,102 | 11/1997 | Gross et al. | 424/450 |
| 5,707,606 | 1/1998 | Quay | 424/9.52 |
| 5,707,607 | 1/1998 | Quay | 424/9.52 |
| 5,711,933 | 1/1998 | Bichon et al. | 424/9.52 |
| 5,716,597 | 2/1998 | Lohrmann et al. | 424/9.5 |
| 5,732,707 | 3/1998 | Widder et al. | 128/661.08 |
| 5,733,527 | 3/1998 | Schutt | 424/9.52 |
| 5,740,807 | 4/1998 | Porter | 128/662.02 |
| 5,804,162 | 9/1998 | Kabalnov et al. | 424/9.51 |
| B1 4,229,360 | 11/1991 | Schneider et al. | 260/403 |

FOREIGN PATENT DOCUMENTS

| | | |
|---|---|---|
| 2 700 952 | 8/1994 | France . |
| 25 21 003 | 8/1976 | Germany . |
| 62-286534 SHO | 12/1987 | Japan . |
| 63-60943 | 3/1988 | Japan . |
| 1044680 | 10/1966 | United Kingdom . |
| 2193095 | 2/1988 | United Kingdom . |
| WO 80/02365 | 11/1980 | WIPO . |
| WO 82/01642 | 5/1982 | WIPO . |
| US85/01161 | 3/1985 | WIPO . |
| WO 86/00238 | 1/1986 | WIPO . |
| WO 86/01103 | 2/1986 | WIPO . |
| WO 89/05040 | 6/1989 | WIPO . |
| WO 90/09152 | 3/1990 | WIPO . |
| WO 90/04384 | 5/1990 | WIPO . |
| WO 90/04943 | 5/1990 | WIPO . |
| WO 91/00086 | 1/1991 | WIPO . |
| WO 91/12823 | 9/1991 | WIPO . |
| WO 91/15244 | 10/1991 | WIPO . |
| WO 92/10166 | 6/1992 | WIPO . |
| WO 92/11873 | 7/1992 | WIPO . |
| WO 92/15284 | 9/1992 | WIPO . |
| WO 92/17212 | 10/1992 | WIPO . |
| WO 92/17213 | 10/1992 | WIPO . |
| WO 92/17436 | 10/1992 | WIPO . |
| WO 92/17514 | 10/1992 | WIPO . |
| WO 92/21382 | 10/1992 | WIPO . |
| WO 92/22249 | 12/1992 | WIPO . |
| WO 92/22298 | 12/1992 | WIPO . |
| WO 93/00933 | 1/1993 | WIPO . |
| WO 93/05819 | 1/1993 | WIPO . |
| WO 93/06869 | 4/1993 | WIPO . |
| WO 93/13809 | 7/1993 | WIPO . |
| WO 93/17718 | 9/1993 | WIPO . |
| WO 93/20802 | 10/1993 | WIPO . |
| WO 94/00110 | 1/1994 | WIPO . |
| WO 94/06477 | 3/1994 | WIPO . |
| WO 94/07539 | 4/1994 | WIPO . |
| WO 94/09829 | 5/1994 | WIPO . |
| WO 84/02909 | 8/1994 | WIPO . |
| WO 94/16739 | 8/1994 | WIPO . |
| WO 94/21302 | 9/1994 | WIPO . |
| WO 94/28780 | 12/1994 | WIPO . |
| WO 94/28873 | 12/1994 | WIPO . |
| WO 95/06518 | 3/1995 | WIPO . |
| WO 95/07072 | 3/1995 | WIPO . |
| WO 95/23615 | 9/1995 | WIPO . |
| WO 95/24184 | 9/1995 | WIPO . |
| WO 96/04018 | 2/1996 | WIPO . |
| WO 96/09793 | 4/1996 | WIPO . |
| WO 96/36286 | 11/1996 | WIPO . |
| WO 96/40281 | 12/1996 | WIPO . |
| WO 98/00172 | 1/1998 | WIPO . |

OTHER PUBLICATIONS

Miller et al., "Physiochemical Approaches to the Mode of Action of General Anesthetics," *J. Amer. Soc. Anesthesiologists,* 36(4):339–351 (1972).

"Properties and Applications of the 'Freon' Fluorocarbons" in DuPont Freon Technical Bulletin B–2 (E.I. DuPont de Nemours and Company, Wilmington, DE), pp. 1–11 (1964).

"'Freon' Fluorocarbons: Properties and Applications" in DuPont Technical Bulletin G–1 (E.I. DuPont de Nemours and Company, Wilmington, DE), pp. 1–10 (1987).

"Encyclopedia of Polymer Science and Engineering," John Wiley & Sons, New York, 1:164–169 (1985).

"Concise Encyclopedia of Polymer Science and Engineering," J. Kroschwitz, ed., John Wiley & Sons, New York, pp. 12–13 (1990).

Wheatley et al., "Contrast Agents for Diagnostic Ultrasound: Development and Evaluation of Polymer–Coated Microbubbles," *Biomaterials,* 11:713–717 (1990).

Fitzpatrick, et al., "Metal Ion Catalyzed Decarboxylation: Kinetics and Mechanism of the Oxidative Decarboxylation of Copper (II) Complexes of Aminomalonic Acid in Aqueous Solution", *Inorganic Chemistry,* vol. 13, No. 3, pp. 568–574 (1974).

Thanassi, "Aminomalonic Acid: Spontaneous Decarboxylation and Reaction with 5–Deoxypyridoxal", *Biochemistry*, vol. 9, No. 3, pp. 525–532 (1970).

Stelmashok et al., *Koordinatsionnaya Khimiya*, vol. 3, No. 4, pp. 524–527 (1977) (Russian and English language versions).

Mayhew et al., "High–Pressure Continuous–Flow System for Drug Entrapment in Liposomes", *Methods in Enzymology*, vol. 149, pp. 64–77 (1987).

Mayhew et al., "Characterization of Liposomes Prepared Using a Microemulsifier", *Biochimica et Biophysica Acta*, vol. 775, pp. 169–174 (1984).

Hope et al., "Production of Large Unilamellar Vesicles by a Rapid Extrusion Procedure: Characterization of Size Distribution, Trapped Volume, and Ability to Maintain a Membrane Potential", *Biochimica et Biophysica Acta*, 812: 55–65 (1985).

Mayer et al., "Vesicles of Variable Size Produced by a Rapid Extrusion Procedure", *Biochimica et Biophysica Acta*, vol. 858, pp. 161–168 (1986).

Cheng, et al., "The Production and Evaluation of Contrast-–Carrying Liposomes Made with an Automatic High Pressure System", *Investigative Radiology*, vol. 22, pp. 47–55 (1987).

Jain, et al., *Introduction to Biological Membranes*, Ch. 9, pp. 192–231 (J. Wiley and Sons, N.Y. 1980).

Sigel, H., ed., *Metal Ions in Biological Systems: Antibiotics and Their Complexes*, vol. 19, (Marcel Dekker, N.Y. 1985).

Nayar et al., "Generation of Large Unilamellar Vesicles From Long–chain Saturated Phosphatidylcholines by Extrusion Technique", *Biochmicia et Biophysica Acta*, vol. 986, pp. 200–206 (1989).

Hope et al., "Generation of Multilamellar and Unilamellar Phospholipid vesicles", *Chemistry and Physics of Lipids*, vol. 40, pp. 89–107 (1986).

Mattrey et al., "Perfluorochemicals as US Contrast Agents for Tumor–Imaging and Hepatosplenography: Preliminary Clinical Results", *Radiology*, vol. 163, pp. 339–343 (1987).

Mattrey et al., "Perfluoroctylbromide: A Liver/Spleen–Specific and Tumor Imaging Ultrasound Contrast material", *Radiology*, vol. 145, pp. 759–762 (1982).

Keller et al., "Successful Left Ventricular Opacification Following Peripheral Venous Injection of Sonicated Contrast Agent: An Experimental Evaluation", *LV Contrast Echocardiography*, vol. 114, No. 3, pp. 570–575 (1987).

Feinstein et al., "Two–Dimensional Contrast Echocardiography, I: In Vitro Development and Quantitative Analysis of Echo Contrast Agents", *JAAC*, vol. 3, No. 1, pp. 14–20 (1984).

Ten Cate et al., "Two–Dimensional Contrast Echocardiography, II: Transpulmonary Studies", *JACC*, vol. 3, No. 1, pp. 21–27 (1984).

Unger et al., "Hepatic Metastases: Liposomal Gd–DTPA–enhanced MR Imaging", *Radiology*, vol. 171, pp. 81–85 (1989).

Deamer et al., "Permeability of Lipid Bilayers to Water and Ionic Solutes", *Chemistry and Physics of Lipids*, vol. 40, pp. 167–188 (1986).

Gutknecht et al., "Diffusion of Carbon Dioxide Through Lipid Bilayer Membranes: Effect of Carbonic Anhydrase, Bicarbonate, and Unstirred Layers", *Chemical Abstracts*, 87:34772q (1977).

Scarpa et al., "Cation Permeability of Liposomes as a Function of the Chemical Composition of the Lipid Bilayers", *Biochimica et Biophysica Acta*, vol. 241, pp. 789–797 (1971).

MacNaughton et al., "Effects of Gaseous Anesthetics and Inert Gases on the Phase Transition in Smectic Mesophases of Dipalmitoyl Phosphatidylcholine", *Biochimica et Biophysica Acta*, vol. 597, pp. 193–198 (1980).

Tilcock et al., "Liposomal Gd–DTPA: Preparation and Characterization of Relaxivity", *Radiology*, vol. 171, pp. 77–80 (1989).

Mann et al., "Formation of Iron Oxides in Unilamellar Vesicles", *Journal of Colloid and Interface Science*, vol. 122, No. 2, pp. 326–335 (1988).

Anderson et al., "Manganese (III) Complexes in Oxidative Decarboxylation of Acids", *J. Am. Chem. Soc.*, vol. 92, No. 8, pp. 2450–2460 (1970).

Muhlradt et al., "Vitamin B6 Analogs: An Improved Synthesis of 5–Deoxypyridoxal", *New Compounds*, vol. 10, pp. 129–130 (1967).

Chapman D., "Physiochemical Properties of Phospholipids and Lipid Water Systems", *Liposome Technology*, Gregoriadis, G., ed., vol. 1, pp. 1–19 (CRC Press, Boca Raton, FL, 1984).

Violante et al., "Particulate Suspensions as Ultrasonic Contrast Agents for Liver and Spleen", *Inv. Rad.*, vol. 23, pp. S294–S297, Sep. 1988.

Fritzsch et al., "Preclinical and Clinical Results with an Ultrasonic Contrast Agent", *Inv. Rad.*, vol. 23, pp. S302–S305, Sep. 1988.

Brochure, *Experience*, Sonicator™, Heat Systems–Ultrasonics, Inc. (1987).

M. Ostro, "Liposomes", Marcel Dekker, New York, pp. 102–103 (1983).

Fukuda et al., "Polymer–Encased Vesicles Derived from Diotadecyldimethylammonium Methacrylate", *J. Am. Chem. Soc.*, vol. 108, pp. 2321–2327 (1986).

Regen, "Polymerized Vesicles", *J. Am. Chem. Soc.*, vol. 102, pp. 6638–6640 (1989).

Rose, A. and Rose, E., "The Condensed Chemical Dictionary", Reinhold Publishing, New York, pp. 728 and 743 (1966).

A.G. Belykh, *Farmakol Toksikol. (MOSC)*, vol. 44(3), pp. 322–326 (1981) (abstract).

J. Vion–Dury et al., *J. Pharmacol. Exper. Ther.*, vol. 250(3), pp. 1113–1118 (1989) (abstract).

M.R. Zalutsky et al., *Invest. Radiol.*, vol. 22(2), pp. 141–147 (1987) (abstract).

Crowe et al., *Archives of Biochemistry and Biophysics*, vol. 242, pp. 240–247 (1985).

Crowe et al., *Archives of Biochemistry and Biophysics*, vol. 220, pp. 477–484 (1983).

Dorland's Illustrated Medical Dictionary, p. 946, 27th ed. (W.B. Saunders Company, Philadelphia 1988).

*Liposome Technology*, Gregoriadis, G., ed., vol. I, pp. 1–18, 29–35, 51–65 and 79–107 (CRC Press Inc., Boca Raton, FL, 1984).

Madden et al., *Chemistry and Physics of Lipids*, vol. 53, pp. 37–46 (1990).

Sinkula et al., *J. Pharm. Sci.*, vol. 64, pp. 181–210 (1975).

Shiina et al., "Hyperthermiaby Low–frequency Synthesized Ultrasound", *IEEE Engineering*, pp. 879–880, vol. 2 (1988) (abstract).

McAvoy et al., *IEEE Engineering, Ultrasonics Symposium Proceedings*, vol. 2, pp. 677–1248 (1989) (abstract).

Chapman et al., "Biomembrane Phase Transitions", *J. Biol. Chem.*, 1974, 249:2512–2521.

Hug et al., "Liposomes for the Transformation of Eukaryotic Cells", *Biochimica et Biophysica Acta*, 1991, 1097:1–17.

Marsh, *CRC Handbook of Lipid Bilayers* (CRC Press, Boca Raton, FL 1990) pp. 139–141.

Szoka et al., "Procedure for Preparation of Liposomes With Large Internal Aqueous Space . . . ", *Proc. Natl. Acad. Sci.* 1978, 75:4194–4198.

Acoustic Imaging: AI5200; Convex Curved Linear Array Ultrasound Transducers Operator's Manual, Nov. 20, 1989, 4700–0003–1C, p. 4.

Bangham et al., "Diffusion of Univalent Ions across the Lamellae of Swollen Phospholipids", *J. Mol. Biol.,* 1965, 13:238–252.

Carson et al., *Ultrasound in Med & Biol.* 3, 1978, 341–350.

Kost et al., *Polymers in Medicine II: Biomedical and Pharmaceutical Applications,* "Ultrasonic Modulated Drug Delivery Systems", Chiellini et al., ed., (Plenum Press, New York and London), pp. 387–396 (1985).

deGier et al., "Relations Between Liposomes and Biomembranes", *Annals of The New York Academy of Sciences,* 1978, 308:85–99.

Felgner et al., "Lipofection: A highly efficient, lipid–mediate DNA–transfection procedure", *Proc. Natl. Acad. Sci.,* 1987, 84:7413–7417.

Gabizon et al., "Liposome formulations with prolonged circulation time in blood and enhanced uptake by tumors", *Proc. Natl. Acad. Sci.,* 1988, 85:6949–6953.

Garelli, et al., *Biochimica et Biophysica Acta,* vol. 1127:41–48 (1992).

Kawai et al., "New Procedure for DNA Transfection with Polycation and Dimethyl Sulfoxide", *Molecular and Cellular Biology,* 1984, 4:1172–1174.

Kuo et al., "Metallocene Antitumor Agents. Solution and Solid–State Molybdenocene Coordination . . . ", *J. Am. Chem. Soc.,* 1991, 113:9027–9045.

*Mammalian Cell Biotechnology: A Practical Approach,* M. Butler, 199 (Oxford University Press, New York), pp. 57–70.

Mathiowitz et al., "Photochemical Rupture of Microcapsules: A Model System", *Journal of Applied Polymer Science,* 1981, 26:809–822.

May et al., "Cationic Liposomes Enable Bovine Herpesvirus Type 2 DNA to Infect Cells", *Acta virol.,* 1991, 35:107.

Poznansky et al., "Biologica Approaches to the Controlled Delivery of Drugs: A Critical Review", *Pharmacol, Rev.,* 1984, 36:277–336.

Sato et al., "Recent Aspects in the Use of Liposomes in Biotechnology and Medicine", *Prog. Lipid Res.* 1992, 4:345–372.

Simons et al., "Antisense c–myb oligonucleotides inhibit intimal arterial smooth muscle cell accumulation in vivo", *Nature,* 1992, 359:67–70.

Thompson, Larry, "At Age 2, Gene Therapy Enters a Growth Phase", *Science* 1992, 258:744–746.

Trubetskoy et al. "Cationic liposomes enhance targeted delivery and expression of exogenous DNA . . . ", Biochimica et Biophysica Acta 1992, 131:311–313.

Umemura et al., "Studies on Sonodynamic Cancer Therapy", *IEEE,* 1992, O–7803–0785, pp. 354–355.

Williams, "Human Gene Therapy: Searching for Better Vectors", *ASM News* [American Society for Microbology] 1992, 58:67–69.

Woodle et al., "Versatility in lipid compositions showing prolonged circulation . . . ", *Biochimica et Biophysica Acta* 1992, 1105:193–200.

Zhou et al., "Targeted delivery of DNA by liposomes and polymers", *J. of Controlled Release* 1992, 19:269–274.

Mathiowitz et al., "Polyanhydride Microspheres as Drug Carriers", *Journal of Applied Polymer Science,* vol. 35, pp. 755–774 (1988).

Sankaram et al., "Cholesterol–Induced Fluid–Phase Immiscibility in Membranes", *Proc. Natl. Acad. Sci.,* vol. 88, pp. 8686–8690 (1991).

*Scientific Apparatus Catalog 92/93* (VWR Scientific, 1991), "Syringes", pp. 1511–1513; "Filtration, Syringe Filters", pp. 766–768; "Filtration, Membranes", pp. 750–753; "Filtration, Filter Holders", p. 744.

Gramiak et al., *Radiology,* "Detection of Intracardiac Blood Flow by Pulsed Echo–Ranging", pp. 415–418 (1971).

Feigenbaum et al., *Circulation,* "Identification of Ultrasound Echoes from the Left Ventricle by Use of Intracardiac Injections of Indocyanine Green", vol. XL1, pp. 615–621 (1970).

Santaella, et al., *FEBS 13463,* "Extended In Vivo Blood Circulation Time of Fluorinated Lipsomes", vol. 336, No. 3, pp. 481–484 (1993).

Brown and Langer, *Annual Review Medicine,* 1988, 39:221 29, Annual Review, Inc., "Transdermal Delivery of Drugs", pp. 221–229.

Moseley, et al., *Microbubbles: A Novel MR Susceptibility Contrast Agent,* abstract, 1991 Napa, California Meeting of the Society for Magnetic Resonance in Medicine.

Ter–Pogossia *Tomography,* Kee, et al., n, "Physical Principles and Instrumentation", *Computed Body* eds., Raven Press, New York, Chapter 1, pp. 1–7 (1988).

Aronberg, "Techniques", *Computed Body Tomography,* Kee, et al., eds., Raven Press, New York, Chapter 2, pp. 9–36 (1988).

Miller, *Ultrasonics* (Sep. 1981), "Ultrasonic detection of resonant cavitation bubbles in a flow tube by their second-–harmonic emissions," pp. 217–224.

Dittrich, "Cardiac Muscle Ischemia and Infarction", The Second Annual International Symposium on Contrast Agents in Diagnostic Ultrasound, Atlantic City, NJ (May 7, 1996) (abstract).

Pantely, "Intravenous Contrast Echocardiography–Tissue Imaging & Quantification of Coronary Blood Flow", The Second Annual International Symposium on Contrast Agents in Diagnostic Ultrasound, Atlantic City, NJ (May 7, 1996) (abstract).

Schutt et al., "Osmotically Stabilized Microbubble Sonographic Contrast Agents",*Acad. Radiol.,* vol. 3, Suppl. 2, pp. S188–S190 (Aug. 1996).

Frézard, et al., "Permeability and stability in buffer and in human serum of fluorinated phospholipid–based liposomes", *Biochimica et Biophysica Acta,* 1192, pp. 61–70 (1994).

Frézard, et al., "Fluorinated Phospholipid–Based Vesicles as Potential Drug Carriers: Encapsulation/Sustaining of Drugs and Stability in Human Serum",*Art, Cells, Blood Subs., and Immob. Biotech.,* 22(4), pp. 1403–1408 (1994).

Chang et al., "Semipermeable Aqueous Microcapsules", *Canadian J. Of Phys. And Pharm.,* 1966, 44, 115–128.

Chang, "Semipermeable Microcapsules", *Science,* 1964, 146, 524–525.

Deasy, *Microencapsulation and Related Drug Processes*, 1983, vol. 20, Chs. 9 and 10, 195–240 (Marcel Dekker, Inc., NY).

Yeung et al., "Preparation of Microencapsulated Liposomes", *J. Microencapsulation*, 1988, 5, 331–337.

Mattrey et al., Gas Emulsions as Ultrasound Contrast Agents; Preliminary Results in Rabbits and Dogs, *Investigative Radiology*, vol. 29, Jun. Supp. 2, pp. S139–S141, 1994.

Meltzer et al., Transmission of Ultrasonic Contrast Through the Lungs, *Ultrasound in Med. & Biol.*, vol. 7, No. 4, 377–384, 1981.

PR Newswire, Apr. 1, 1986.

Swanson et al., Chapter 22, "Enhancement Agents for Ultrasound: Fundamentals", *Pharmaceuticals In Medical Imaging*, pp. 682–687 (1990).

Ophir et al., "Contrast Agents in Diagnostic Ultrasound", *Ultrasound in Med. & Biol.*, vol. 15, No. 4, pp. 319–333 (1989).

Jacobs, "Intraocular gas measurement using A-scan ultrasound", *Current Eye Research*, vol. 5, No. 8, pp. 575–578 (1986).

Lincoff et al., "Intravitreal Expansion of Perfluorocarbon Bubbles", *Arch. Ophthalmol.*, 1980, 98, 1646.

Lincoff et al., "Intravitreal Longevity of Three Perfluorocarbon Gases", *Arch. Ophthalmol.*, 1980, 98, 1610–1611.

Lincoff et al., "The Perfluorocarbon Gases in the Treatment of Retinal Detachment", *Opthalmology*, 1983, 90(5), 546–551.

Gardner et al., "A Survey of Intraocular Gas Use in North America", *Arch. Ophthalmol.*, 1988, 106, 1188–1189.

Unger et al., "Liposomal MR Contrast Agents", *J. Liposome Research*, 1994, 4(2), 811–834.

Hynynen et al., "The Usefulness of a Contrast Agent and Gradient Recalled Acquisition in a Steady–State Imaging Sequence for Magnetic Resonance Imaging–Guided Non-invasive Ultrasound Surgery", *Investigative Radiology*, 1994, 29(10), 897–903.

Lindner et al., "Myocardial Perfusion Characteristics and Hemodynamic Profile of MRX–115, a Venous Echocardiographic Contrast Agent, During Acute Myocardial Infarction", *J. Am. Soc. Echocardiography*, 1998, 11(1), 36–46.

Regen et al., "Polymerized Phosphatidylcholine Vesicles. Synthesis and Characterization", *J. Am. Chem. Soc.*, 1982, 104(3), 191–195.

Wei et al., "Quantification of Myocardial Blood Flow with Ultrasound–Induced Destruction of Microbubbles Administered as a Constant Venous Infusion", *Circulation*, 1998, 97, 473–483.

Nomura et al., "US Contrast Enhancement of Hepatic Tumor with Helium Gas Microbubbles: A Preliminary Report", *Jpn. J. Med. Ultrasonics*, 1991, 18(5), (Japanese with English language abstract).

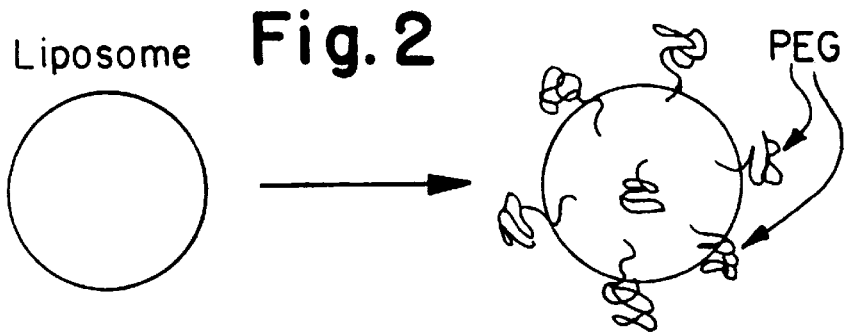
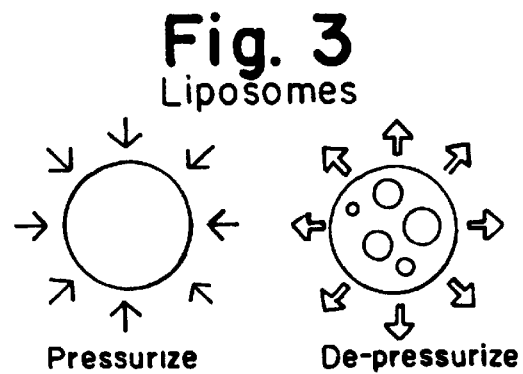
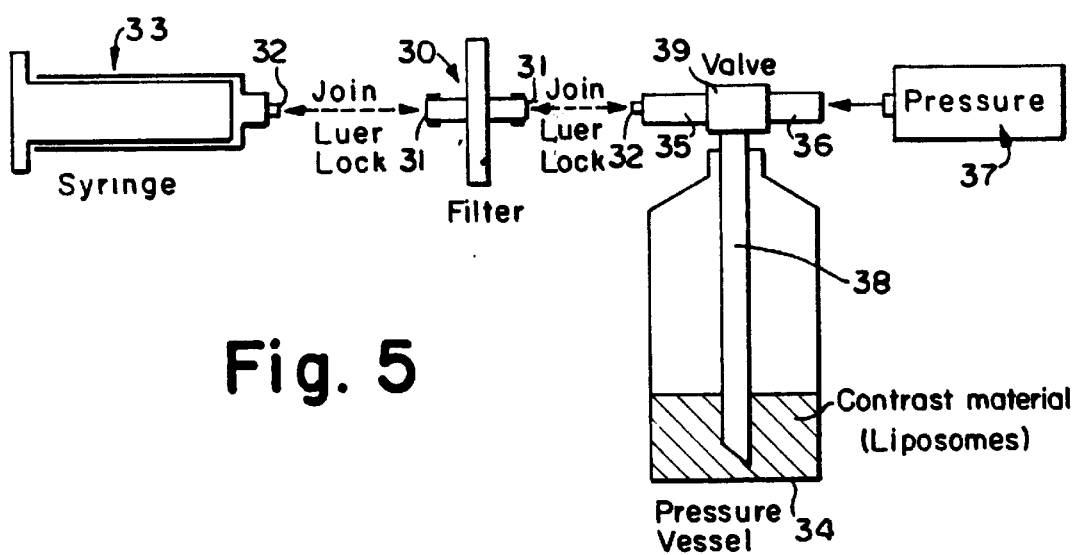

CONTRAST AGENTS FOR ULTRASONIC IMAGING AND METHODS FOR PREPARING THE SAME

RELATED APPLICATION

This application is a divisional of U.S. application Ser. No. 08/655,719, filed Jun. 18, 1996, which is a divisional of U.S. application Ser. No. 08/468,056, filed Jun. 6, 1995, now U.S. Pat. No. 5,571,497, which is a divisional of U.S. application Ser. No. 08/395,683, filed Feb. 28, 1995, now U.S. Pat. No. 5,456,901, which is a divisional of U.S. application Ser. No. 08/163,039, filed Dec. 6, 1993, which is a divisional of U.S. application Ser. No. 08/085,608, filed Jun. 30, 1993, now U.S. Pat. No. 5,334,381, which is a divisional of U.S. application Ser. No. 08/018,112, filed Feb. 17, 1993, now abandoned, which is a divisional of U.S. application Ser. No. 07/967,974, filed Oct. 27, 1992, now U.S. Pat. No. 5,352,435, which is a divisional of U.S. application Ser. No. 07/818,069, filed Jan. 8, 1992, now U.S. Pat. No. 5,230,882, which is a divisional of U.S. application Ser. No. 07/750,877, filed Aug. 26, 1991, now U.S. Pat. No. 5,123,414, which is a divisional of U.S. application Ser. No. 07/569,828, filed Aug. 20, 1990, now U.S. Pat. No. 5,088,499, which is a continuation-in-part of U.S. Ser. No. 455,707, filed Dec. 22, 1989 now abandoned.

BACKGROUND OF THE INVENTION

1. Field of the Invention

This invention relates to the field of ultrasonic imaging, and, more specifically, to the use of liposomes in ultrasonic imaging procedures.

2. Background of the Invention

There are a variety of imaging techniques which have been used to detect and diagnose disease in animals and humans. One of the first techniques used for diagnostic imaging was X-rays. The images obtained through this technique reflect the electron density of the object being imaged. Contrast agents such as barium or iodine are used to attenuate or block X-rays such that the contrast between various structures is increased. For example, barium is used for gastrointestinal studies to define the bowel lumen and visualize the mucosal surfaces of the bowel. Iodinated contrast media is used intravascularly to visualize the arteries and this is called angiography. X-rays, however, are known to be dangerous. The radiation employed in X-rays is ionizing and the deleterious effects of the ionizing radiation are cumulative.

Magnetic resonance imaging (MRI) is another important imaging technique, however it has the drawbacks of expense and the fact that it cannot be conducted as a portable examination. In addition, MRI is not available at many medical centers.

Radionuclides, employed in nuclear medicine, provide another imaging technique. In employing this technique, radionuclides such as technetium labelled compounds are injected into the patient, and images are obtained from gamma cameras. Nuclear medicine techniques, however, suffer from poor spatial resolution and expose the animal or patient to the deleterious effects of radiation. Furthermore, there is a problem with the handling and disposal of radionuclides.

Ultrasound, another diagnostic imaging technique, is unlike nuclear medicine and X-rays in that it does not expose the patient to the harmful effects of ionizing radiation. Moreover, unlike magnetic resonance imaging, ultrasound is relatively inexpensive and can be conducted as a portable examination. In using the ultrasound technique, sound is transmitted into a patient or animal via a transducer. When the sound waves propagate through the body, they encounter interfaces from tissues and fluids. Depending on the reflectivity and acoustic properties of the tissues and fluids in the body, the ultrasound sound waves are either reflected or absorbed. When sound waves are reflected by an interface they are detected by the receiver in the transducer and processed to form an image. The acoustic properties of the tissues and fluids within the body determine the contrast which appears in the resultant image.

Advances have been made in recent years in ultrasound technology. However, despite these various technological improvements, ultrasound is still an imperfect tool in a number of respects, particularly with respect to the detection of disease in the liver and spleen, kidneys and vasculature and in measuring blood flow. The ability to detect and measure these things depends on the difference in acoustic properties between blood or other tissues and the surrounding tissues. As a result, contrast agents have been sought which will increase the acoustic difference between blood and surrounding tissues in order to improve the measurement of blood flow, or between one tissue and another such as between the liver and a tumor in order to improve disease detection.

The principles underlying image formation in ultrasound have directed researchers to this pursuit of contrast agents. When sound waves from ultrasound pass through a substance, the acoustic properties of that substance will depend upon the velocity of the sound and the density of that substance. Changes in the acoustic properties or acoustic impedance of the substance are most pronounced at interfaces of different substances with greatly different density or acoustic impedance, particularly at the interface between solids, liquids and gases. When the ultrasound sound waves encounter such interfaces, the changes in acoustic impedance result in a more intense reflection of sound waves and a more intense signal in the ultrasound image.

Many of the prior art contrast agents developed to date for ultrasound have comprised liquids containing microbubbles of gas where the microbubbles have been encapsulated with gelatin or saccharine. Those microbubble and gelatin/saccharine constructs have most often been prepared using agitation techniques. Other prior art is directed to attempts with protein-associated air bubbles or air bubbles incorporated in microspheres composed of either albumin or collagen. Furthermore, heavy metal particulates have been evaluated as ultrasound contrast agents. There have also been some reports of liposomes described as useful in ultrasonic applications having gas or gaseous precursors encapsulated therein.

While the prior art has produced some ultrasound contrast agents which are echogenic on ultrasound, that is, provide a contrast enhancement signal, the contrast agents developed thus far have various problems. The protein based air bubble systems have the drawback that a foreign protein which may be antigenic and potentially toxic is being employed. The liposomal contrast agents have had problems with uneven size distribution and poor stability. The gaseous precursor containing liposomes have also been inefficient in their ability to form contrast enhancing gas in vivo. Moreover, while some of the prototype prior art contrast agents have demonstrated echogenic effects as transpulmonary vascular contrast agents, many of these agents have failed to demonstrate a convincing effect on improving tumor imaging in, for example, the liver or spleen. Furthermore, many of the methods for preparing these ultrasound contrast agents, particularly the gas encapsulated liposomes, are inefficient, expensive, and otherwise unsatisfactory.

The present invention is directed to answering these and other important needs.

SUMMARY OF THE INVENTION

In one embodiment, the present invention is directed to a contrast agent for ultrasonic imaging comprising an ionophore-containing liposome having encapsulated therein a pH-activated gaseous precursor.

In another embodiment, the present invention is directed to a contrast agent for ultrasonic imaging which comprises a liposome having encapsulated therein a photo-activated gaseous precursor.

In a third embodiment, the present invention is directed to a contrast agent for ultrasonic imaging which comprises a liposome having encapsulated therein a temperature-activated gaseous precursor.

In a further embodiment, the present invention is directed to a contrast agent for ultrasonic imaging which comprises a liposome having encapsulated therein a solid or liquid contrast enhancing agent.

An even further embodiment of the invention is directed to a method for imaging a patient using ultrasound comprising administering to the patient a liposome of the invention and scanning the patient using ultrasound.

In a still further embodiment, the present invention comprises novel methods for encapsulating a gas within the internal space of a liposome to produce contrast agents for ultrasonic imaging.

The contrast agents embodied within the present invention are echogenic, that is, capable of reflecting ultrasound waves to enhance signal intensity on an ultrasound image. In certain preparations particularly designed as intravascular contrast agents, the present contrast agents are small enough to pass through the capillaries of pulmonary circulation and are effective in providing good contrast enhancement of the heart, arterial system and venous system. In other preparations designed for injecting into other structures or cavities, the vesicles are larger to maximize echogenicity and provide highly effective contrast enhancement. In accordance with the present invention, the liposomes with the gas, gaseous precursors and/or solid or liquid contrast enhancing agents encapsulated therein can be produced in defined and reproducible sizes. The present invention also allows targeting and delivery of the contrast agent to specific sites such as the vasculature, liver, spleen and kidney. The present invention is free from the toxicity associated with the use of foreign proteins to encapsulate air bubbles and also minimizes the likelihood of embolisms occurring. In addition, the liposomes of the present invention are capable of long term storage. Moreover, the novel methods of the invention for encapsulating gas within the internal space of a liposome are highly efficient and inexpensive to carry out.

The liposomal ultrasound contrast agents of the invention permit advanced imaging of organs and tissues in a way not previously contemplated. Because liposome membranes can be optimized for blood pool or circulation half-life, effective perfusion and blood pool contrast agents will be available. This will be useful in the heart, for example, for diagnosing ischemia and in other organs for diagnosing decreased blood flow or shunts. In blood pool lesions such as cavernous hemangioma, these agents will be useful for making accurate diagnoses. Because these agents can be optimized for uptake by healthy cells in organs such as the liver and spleen, the contrast agent facilitates the ultrasonic detection and characterization of tumors in these organs.

These and other features of the invention and the advantages thereof will be further described in the drawings and description below.

BRIEF DESCRIPTION OF THE FIGURES

FIG. 2. In this figure is illustrated one method of modifying the surface of a liposome with polymer such as polyethylene glycol (PEG), so as to be able to modulate the clearance and biodistribution kinetics of the liposomes with entrapped gas, gaseous precursors and/or solid or liquid contrast enhancing agents.

FIG. 3. This figure illustrates the basic pressurization and depressurization phenomenons behind some of the devices and methods for preparing the gas-containing liposomes of the invention. First, liposomes are added to a vessel, and the vessel is then pressurized with gas. Under pressure, the gas goes into solution and passes across the liposome membranes. When the pressure is released, gas bubbles form within the liposomes.

FIG. 5. This figure illustrates another apparatus of the invention for synthesizing liposomes having encapsulated therein a gas. A syringe in which liposomes have been placed is connected via one or more filters of various pore sizes to an inlet/outlet port and valve of the pressure vessel. The syringe is then emptied through the filters and the inlet/outlet port and valve into the bottom of the vessel. Alternatively, the vessel may be directly loaded with the liposomes without using the syringe and/or filters, and/or inlet/outlet port and valve. The vessel is then pressurized with a gas, resulting in a gas-containing liposome composition. The gas-containing liposome contents of the vessel may then be discharged through the inlet/outlet port and valve and the filter assembly, and emptied into the syringe. Alternatively, the liposome may be removed directly without passing through the filter and/or inlet/outlet port and valve and/or emptying into the syringe.

DETAILED DESCRIPTION OF THE INVENTION

In one embodiment, the present invention provides a contrast agent for ultrasound imaging which comprises an ionophore-containing liposome having encapsulated therein a pH-activated gaseous precursor.

As used herein, the phrase "ionophore-containing liposome" denotes a liposome having incorporated in the membrane thereof an ionophore. The term "ionophore", as used herein, denotes compounds which are capable of facilitating the transport of hydrogen ions or hydroxide ions across the liposome membrane to effect a change in pH inside the liposome membrane, and include compounds commonly referred to as proton carriers and channel formers. Suitable ionophores include proton carriers such as nitro-, halo- and oxygenated phenols and carbonylcyanide phenylhydrazones. Preferred of such proton carriers are carbonylcyanide, p-trifluoromethoxyphenylhydrazone (FCCP), carbonylcyanide M-chlorophenylhydrazone (CCCP), carbonylcyanide phenylhydrazine (CCP), tetrachloro-2-trifluoromethyl benzimidazole (TTFB), 5,6-dichloro-2-trifluoromethyl benzimidazole (DTFB), and Uncoupler 1799 Suitable channel formers include gramicidin, alamethicin, filipin, etruscomycin, nystatin, pimaricin, and amphotericin. Other suitable proton carriers include the following compounds which preferably exhibit selectivity for cations, but will also transport protons and/or hydroxide ions: valinomycin, enniatin (type A, B or C), beauvericin, monomycin, nonactin, monactin, dinactin, trinactin, tetranactin, antamanide, nigericin, monensin, salinomycin, narisin, mutalomycin, carriomycin, dianemycin, septamycin, A-204 A, X-206, X-537 A (lasalocid), A-23187 and dicyclohexyl-18-crown-6. Such ionophores are well known in the art and are described, for example in Jain et al., *Introduction to Biological Membranes*, (J. Wiley and Sons, N.Y. 1980), especially pp. 192–231, and *Methyl Ions In Biological Systems*, ed. H. Sygel, Vol. 19, "Antibiotics And Their Complexes" (Dekker, N.Y. 1985), disclosures of each of which are incorporated herein by reference in their entirety. The ionophores may be used alone or in combination with one another.

Figure 1A:
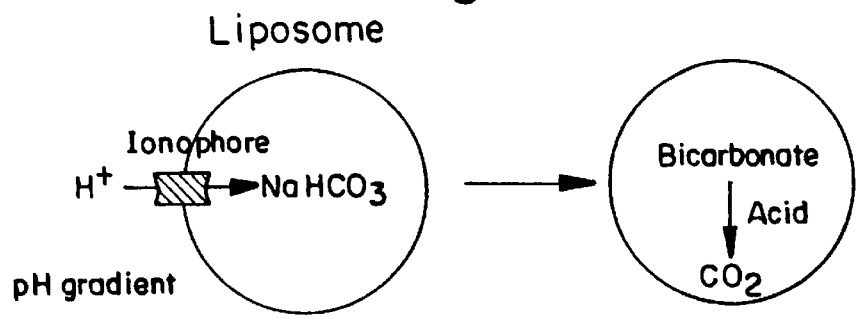
FIG. 1A. In this figure, the general method in which a gaseous precursor reacts to form a gas in response to a change in pH within a vesicle is described. In the example illustrated, bicarbonate salts are entrapped within the interior aqueous space of the vesicle and an ionophore such as, for example, p-trifluoromethoxy-carbonylcyanide phenylhydrazone is present within the liposome membrane matrix to promote hydrogen ion flux across the liposomal membrane. The pH change within the vesicle interior facilitated by the ionophore results in the formation of a highly echogenic carbon dioxide gas.

It has been found that although liposomes are not impermeable to protons or hydroxide ions, the permeability coefficient of liposomes is generally so very low that it often takes weeks or months to dissipate a pH gradient. Providing a more rapid transport of hydrogen ions or hydroxide ions across a liposome membrane in order to activate pH- modulated gaseous precursors is necessary. The incorporation of ionophores in the liposome membrane, in accordance with the present invention, provides the necessary means of transporting the activating ions. By increasing the rate of hydrogen or hydroxide ion flux across the liposome membrane, such ionophores will increase the rate within the liposome of gas formation from the pH-activated gaseous precursor. This phenomenon is diagrammatically represented in FIG. 1A.

The phrase "pH-activated gaseous precursor", as used herein, denotes a compound in solid or liquid form which, when exposed to a drop in pH, will form a gas. As noted above, this concept is illustrated in FIG. 1A. Such compounds include, but are not limited to, metal carbonate and bicarbonate salts, such as the alkali metal carbonates and bicarbonates, and the alkaline earth carbonates and bicarbonates, and mixtures thereof. Exemplary of such compounds are lithium carbonate, sodium carbonate, potassium carbonate, lithium bicarbonate, sodium bicarbonate, potassium bicarbonate, magnesium carbonate, calcium carbonate, magnesium bicarbonate, and the like. Also useful gas generating compounds are ammonium carbonate, ammonium bicarbonate, ammonium sesquecarbonate, sodium sesquecarbonate, and the like. These compounds, when dissolved in water, show a pH of greater than about 7, usually between about 8 and about 12. Other pH-activated gaseous precursors include aminomalonate, which, when dissolved in water, generally shows a pH of about 5 to 6. The pka1 of aminomalonate is 3.32 and the pka2 is 9.83. Aminomalonate is well known in the art, and its preparation is described, for example, in Thanassi, *Biochemistry*, Vol. 9, no. 3, pp. 525–532 (1970), Fitzpatrick et al., *Inorganic Chemistry*, Vol. 13, no. 3, pp. 568–574 (1974), Stelmashok et al., *Koordinatsionnaya Khimiya*, Vol. 3, no. 4, pp. 524–527 (1977). Other suitable pH-activated gaseous precursors will be apparent to those skilled in the art.

As those skilled in the art would recognize, such compounds can be activated prior to administration, if desired. Of course, by choosing a gaseous precursor with the appropriate pKa, one skilled in the art can prepare a liposome whereby gas will form in the liposome after intravenous injection or injection into a body cavity. Even when exposure to the appropriate pH occurs prior to administration, an advantage is achieved in that the liposome with the gaseous precursor is a more stable entity than a liposome which has been placed on the shelf with a gas encapsulated therein. Accordingly, greater shelf life is evident from the use of liposomes which encapsulate a pH-activated gaseous precursor. It has also been discovered that the use of ionophores allows liposomes entrapping pH-activated gaseous precursors to efficiently produce gas when exposed to a pH gradient. The resulting gas-containing liposomes are capable of being detected easily in vivo because of their lower density as compared to the surrounding bodily structures and organs.

Figure 1B:
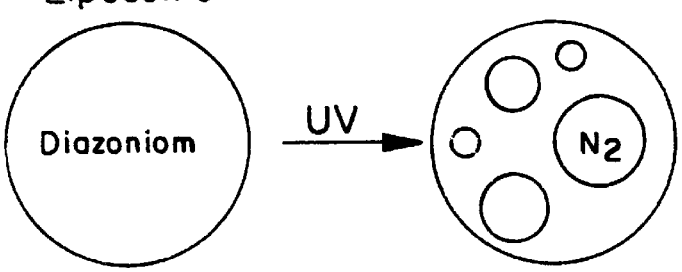
FIG. 1B. In this figure, the general method in which a gaseous precursors reacts to form gases upon exposure to UV light is described. In the specific example illustrated, diazonium compounds trapped inside the lipid vesicles form a highly echogenic nitrogen gas as a result of UV exposure.

In a second embodiment of the invention, a contrast agent for ultrasonic imaging is provided which comprises a liposome having encapsulated therein a photo-activated gaseous precursor. As used herein, the phrase "photo-activated gaseous precursor" denotes a light sensitive chemical which forms a gas after exposure to such light. This concept is illustrated in FIG. 1B. Suitable photosensitive compounds include diazonium compounds which decompose to form nitrogen gas after exposure to ultraviolet light. Another suitable compound is aminomalonate. As one skilled in the art would recognize, other gaseous precursors may be chosen which form gas after exposure to light. Depending upon the application, exposure to such light may be necessary prior to in vivo administration, or in some instances can occur subsequent to in vivo administration. Even when exposure to the appropriate light occurs prior to administration, an advantage is achieved in that the liposome with the gaseous precursor is a more stable entity than a liposome which has been placed on the shelf with a gas encapsulated therein. Accordingly, greater shelf life is evident from the use of the liposome which encapsulates a photo-activated gaseous precursor. The resulting gas-containing liposomes are capable of being detected easily in vivo because of their lower density as compared to the surrounding bodily structures and organs.

Figure 1C:
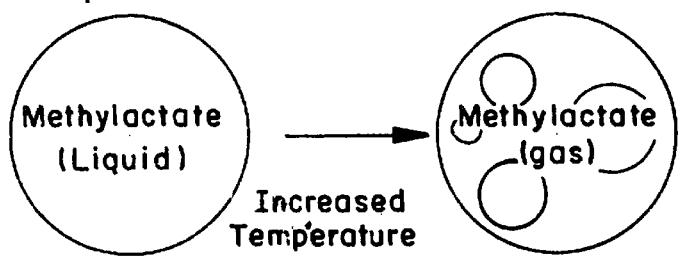
FIG. 1C. In this figure, the general method in which a gaseous precursor forms a gas in response to an increase in temperature, is illustrated. Once injected into a patient, methylactate, for example, is transformed from a liquid to a highly echogenic gas as a result of the increase in temperature from room temperature to physiological temperature.

In a third embodiment, the present invention is directed to a contrast agent for ultrasonic imaging which comprises a liposome having encapsulated therein a temperature-activated gaseous precursor. As used herein, the phrase "temperature-activated gaseous precursor" denotes a compound which forms a gas following a change in temperature. This concept is illustrated in FIG. 1C. Suitable temperature-activated gaseous precursors are well known to those skilled in the art, and include, for example, methylactate, a compound which is in a liquid phase at ambient temperatures, but which forms a gas at physiological temperatures. As those skilled in the art would recognize, such compounds can be activated prior to administration or, as in the case of methylactate, can be activated upon injection into the patient. Even when exposure to the appropriate temperature occurs prior to administration, an advantage is achieved in that the liposome with the gaseous precursor is a more stable entity than a liposome which has been placed on the shelf with a gas encapsulated therein. Accordingly, greater shelf life is evident from the use of the liposome which encapsulates a temperature-activated gaseous precursor. The resulting gas-containing liposomes are capable of being detected easily in vivo because of their lower density as compared to the surrounding bodily structures and organs. In addition, as those skilled in the art would recognize, such temperature sensitive gas-forming liposomes can be used as indicators of in vivo temperature.

Liposomes encapsulating solid and liquid contrast enhancing agents are also encompassed within the subject invention. As used herein, the terms "solid contrast enhancing agent" and "liquid contrast enhancing agent", denotes solid particulate materials, and solubilized or liquid materials, respectively, which are echogenic on ultrasound. Suitable solid contrast enhancing agents will be readily apparent to those skilled in the art once armed with the present disclosure, and include magnetite ($Fe_3O_4$), solid iodine particles such as particles formed from iodipamide ethyl ester, and particles formed by precipitating a water insoluble derivative of the ionic iodinated contrast medium metricate. Suitable liquid contrast enhancing agents will be readily apparent to those skilled in the art, once armed with the present disclosure, and include solubilized iodinated contrast agents. The latter is preferably used as an intravascular contrast agent for the purpose of visualizing flow, but is also highly effective for detecting tumors in the liver and spleen.

Figure 1D:
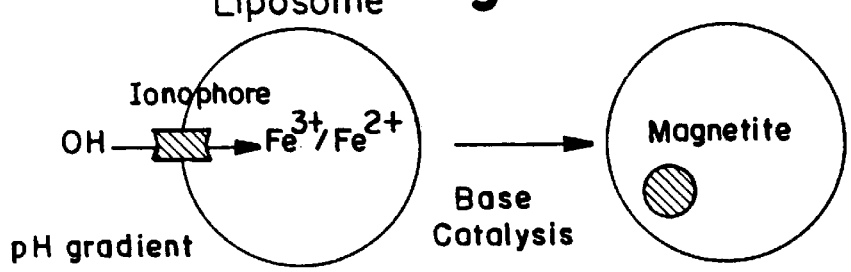
FIG. 1D. In this figure, one method of entrapping a particulate solid contrast enhancing agent such as magnetite, within a liposome is described. In the illustrated method, a mixture of ferrous and ferric salts is entrapped within the aqueous core of the liposome. An ionophore such as valinomycin is incorporated within the matrix of the liposome in order to increase the rate of proton flux across the membrane. Prior to or during use, the pH on the exterior of the vesicle is then increased by the addition of the appropriate alkali resulting in an increase in the pH in the interior of the liposome. The increase in pH in turn promotes base catalysis which results in the in situ formation of highly echogenic magnetite within the liposome. It is equally possible to entrap preformed solid contrast enhancing agents such as preformed magnetite in the liposomes.

As those skilled in the art will recognize upon reading the present disclosure, some solid and liquid contrast enhancing agents can be formed in situ. In the case of magnetite, for example, iron salts can be encapsulated at low pH (e.g., pH 2) and the external pH of the outside solution raised. The iron oxides then precipitate within the vesicle forming magnetite. To facilitate the transport of hydroxide ion into the vesicle, an ionophore such as valinomycin is incorporated into the liposome membrane. This is similar to the situation shown in FIG. 1D, except that in this instance, pH is being raised, rather than lowered.

The liposomes employed in the present invention can be prepared using any one of a variety of conventional liposome preparatory techniques. As will be readily apparent to those skilled in the art, such conventional techniques include sonication, chelate dialysis, homogenization, solvent infusion coupled with extrusion, freeze-thaw extrusion, microemulsification, as well as others. These techniques, as well as others, are discussed, for example, in U.S. Pat. No. 4,728,578, U.K. Patent Application G.B. 2193095 A, U.S. Pat. No. 4,728,575, U.S. Pat. No. 4,737,323, International Application PCT/US85/01161, Mayer et al., *Biochimica et Biophysica Acta*, Vol. 858, pp. 161–168 (1986), Hope et al., *Biochimica et Biophysica Acta*, Vol. 812, pp. 55–65 (1985), U.S. Pat. No. 4,533,254, Mahew et al., *Methods In Enzymology*, Vol. 149, pp. 64–77 (1987), Mahew et al., *Biochimica et Biophysica Acta*, Vol. 75, pp. 169–174 (1984), and Cheng et al., *Investigative Radiology*, Vol. 22, pp. 47–55 (1987), and U.S. Ser. No. 428,339, filed Oct. 27, 1989. The disclosures of each of the foregoing patents, publications and patent applications are incorporated by reference herein, in their entirety. As a preferred technique, a solvent free system similar to that described in International Application PCT/US85/01161, or U.S. Ser. No. 428,339, filed Oct. 27, 1989, is employed in preparing the liposome constructions. By following these procedures, one is able to prepare liposomes having encapsulated therein a gaseous precursor or a solid or liquid contrast enhancing agent.

The materials which may be utilized in preparing the liposomes of the present invention include any of the materials or combinations thereof known to those skilled in the art as suitable in liposome construction. The lipids used may be of either natural or synthetic origin. Such materials include, but are not limited to, lipids such as cholesterol, phosphatidylcholine, phosphatidylethanolamine, phosphatidylserine, phosphatidylglycerol, phosphatidicacid, phosphatidylinositol, lysolipids, fatty acids, sphingomyelin, glycosphingolipids, glucolipids, glycolipids, sulphatides, lipids with ether and ester-linked fatty acids, polymerizable lipids, and combinations thereof. As one skilled in the art will recognize, the liposomes may be synthesized in the absence or presence of incorporated glycolipid, complex carbohydrate, protein or synthetic polymer, using conventional procedures. The surface of a liposome may also be modified with a polymer, such as, for example, with polyethylene glycol (PEG), using procedures readily apparent to those skilled in the art. This is illustrated in FIG. 2. Any species of lipid may be used, with the sole proviso that the lipid or combination of lipids and associated materials incorporated within the lipid matrix should form a bilayer phase under physiologically relevant conditions. As one skilled in the art will recognize, the composition of the liposomes may be altered to modulate the biodistribution and clearance properties of the resulting liposomes.

To incorporate ionophores into the liposome membrane, the ionophores, which are lipophilic, are simply added to the lipid mixture, and the liposomes are prepared in the usual fashion.

In addition, the size of the vesicles can be adjusted by a variety of procedures including filtration, sonication, homogenization and similar methods to modulate liposomal biodistribution and clearance. To increase internal aqueous trap volume, the vesicles can be subjected to repeated cycles of freezing and thawing.

The liposomes of the invention may be of varying sizes, but preferably have a mean outer diameter between about 30 nanometers and about 10 microns. As is known to those skilled in the art, vesicle size influences biodistribution and, therefore, different size vesicles are selected for various purposes. For intravascular use, for example, vesicle size is generally no larger than about 2 microns, and generally no smaller than about 30 nanometers, in mean outer diameter. In the size range of 2–3 microns, the vesicles are by their nature multilamellar. Within this range, to maximize echogenicity with a liposomal contrast agent which has a short intravascular half life, larger vesicles are selected, e.g., about 1 to about 2 microns in mean outer diameter. For sustained blood pool imaging such as for perfusion, smaller vesicles are used, e.g., between about 100 nanometers and several hundred nanometers in mean outer diameter. To provide ultrasound enhancement of organs such as the liver and to allow differentiation of tumor from normal tissue smaller vesicles between about 30 nm and about 100 nm in mean outer diameter which will cross the capillary fenestrations into the liver and increase the uptake by liver may be employed. For imaging of body cavities and non-vascular injection, larger vesicles, e.g., between about 2 and about 10 micron mean outside diameter may be employed to maximize echogenicity of entrapped air.

The lipids employed in the preparations are selected to optimize the particular diagnostic use, minimize toxicity and maximize shelf-life of the product. Neutral vesicles composed of phosphatidylcholine and cholesterol function quite well as intravascular contrast agents to entrap gas, magnetite, solid iodine particles and solubilized iodinated contrast agents. To improve uptake by cells such as the reticuloendothelial system (RES), a negatively charged lipid such as phosphatidylglycerol, phosphatidylserine or similar materials is added. To prolong the blood pool half life, highly saturated lipids which are in the gel state at physiological temperature such as dipalmitoylphosphatidylcholine are used. For even greater vesicle stability and prolongation of blood pool half-life the liposome can be polymerized using polymerizable lipids, or the surface of the vesicle can be coated with polymers such as polyethylene glycol so as to protect the surface of the vesicle from serum proteins, or gangliosides such as GM1 can be incorporated within the lipid matrix.

The pH-activated gaseous precursor, the photo-activated gaseous precursor, the temperature-activated gaseous precursor, and/or the solid or liquid contrast enhancing agent can be incorporated into the liposome by being added to the medium in which the liposome is being formed, in accordance with conventional protocol.

The liposomes of the present invention are useful in ultrasound imaging.

In a still further embodiment, the present invention comprises novel devices and methods for encapsulating a gas within the internal space of the liposome. The liposomes thus produced are also useful in ultrasound imaging.

In general terms, in using the device and carrying out the method of the invention, liposomes are added to a vessel, and the vessel is then pressurized with gas. Under pressure, the gas goes into solution and passes across the liposome membranes. When the pressure is released, gas bubbles form within the liposomes. FIG. 3 illustrates the general pressurization and depressurization phenomenons of the invention.

In using the pressurization devices and carrying out the pressurization processes of the invention, it is preferable to utilize a liposome that does not contain a sterol as part of the membrane. The presence of sterols such as cholesterol in the liposome membrane, particularly if they are present in significant quantities, i.e., greater than about 5% of the membrane by volume, tends to substantially inhibit the flow of certain solubilized gases, such as carbon dioxide, across the liposome membrane. Also, if the membrane is comprised largely of saturated lipids, that is greater than about 80% saturated lipids, the flow of certain solubilized gases, such as that of carbon dioxide, is also substantially inhibited.

The liposomes may or may not be pre-sized prior to being placed within the pressurization vessel. In the case of pre-sizing this may be achieved by a variety of means including, but not limited to, sonication, gel-filtration, filtration through polystyrene or polycarbonate filters or other filters of suitable material, French press or microemulsification methods.

Figure 4:
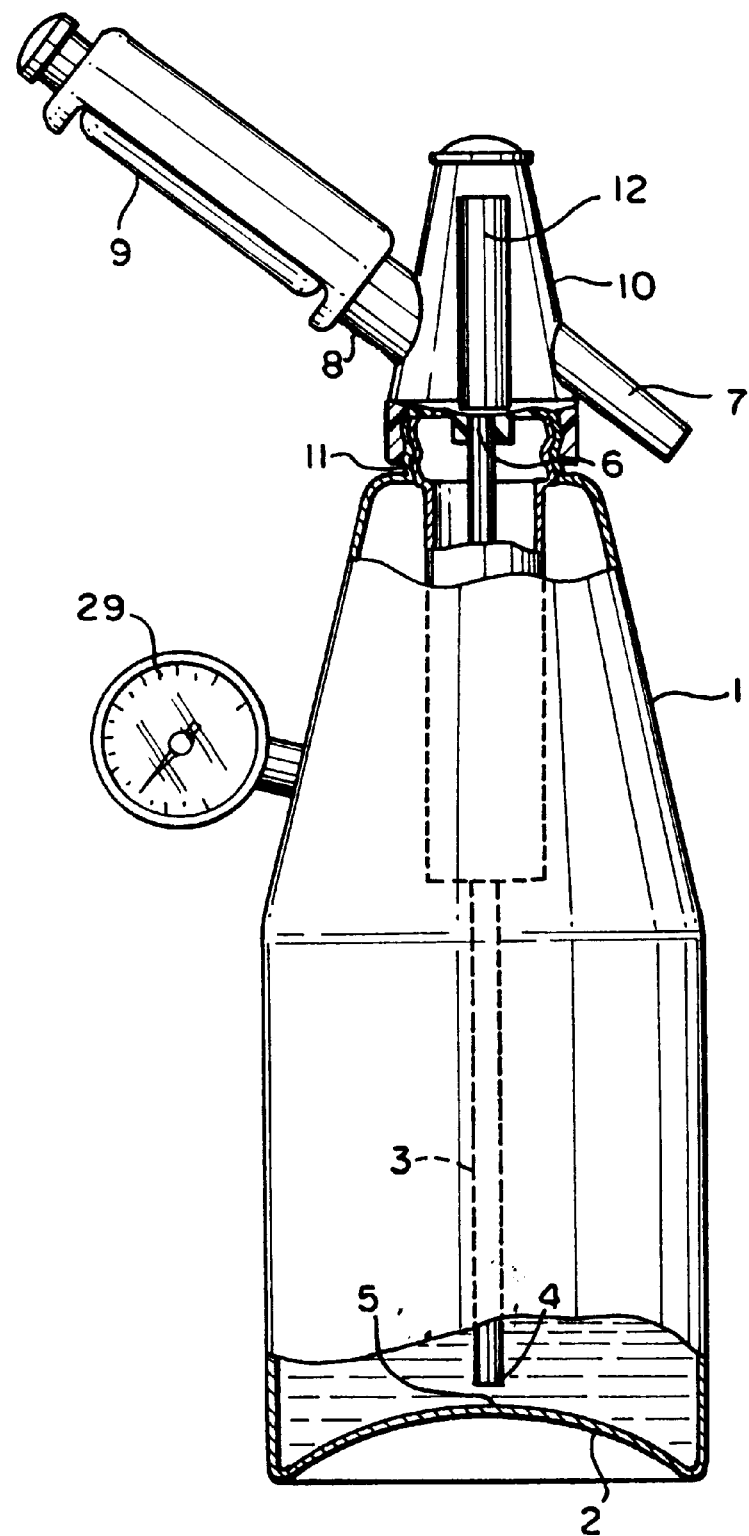
FIG. 4. This figure illustrates one apparatus of the invention for synthesizing liposomes having encapsulated therein a gas. The apparatus is utilized by placing a liquid media which contains liposomes into the vessel. A cap is then threaded onto the vessel opening providing a pressure tight seal. The vessel is pressurized by fitting a cartridge containing a gas, such as carbon dioxide, into an inlet port. The cartridge discharges its contents into the upper end of a tube fitted into the vessel. The gas flows through the tube and exits at the lower end of the tube into the bottom of the vessel. After the gas has been introduced into the vessel, the vessel can then be depressurized by ejecting the liquid from the vessel.

There is shown is FIG. 4 an apparatus for synthesizing liposomes having encapsulated therein a gas. The apparatus is, in essence, a modified soda seltzer bottle. The apparatus is utilized by placing a liquid media, such as a phosphate buffered saline solution which contains liposomes, into a vessel (1). Typically, the liposomes will be comprised of egg phosphatidylcholine, although as described above, other lipids can be employed in the preparation of the liposomes. A cap (10) is then threaded onto the vessel opening (11), providing a pressure tight seal. The vessel is pressurized by fitting a cartridge (9) containing a gas or a combination of gases, such as carbon dioxide, into an inlet port (8). The vessel may be constructed of any suitable material, such as glass or acrylic, and may be disposable, if desired. The cartridge discharges its contents into the upper end (6) of a tube (3), preferably a polyethylene tube, fitted into the vessel (1). The gas flows through the tube and exits at the lower end (4) of the tube. The gas then bubbles upward through the liquid media so that at least a portion of the gas dissolves in the liquid media. Generally, the pressure of the gas in this and other pressurization devices and methods disclosed herein, is between about 2 and about 400 psi. In the preferred embodiment, the vessel is pressurized to between the 50–120 psi range. Within this range, generally higher pressures are preferred for certain gases, such as nitrogen, and gradually lower pressures required for others, such as carbon dioxide. If necessary, additional gas cartridges may be used. A pressure gauge (29) indicates the pressure in the vessel.

The liposome membranes are permeable to the pressurized gas. Thus, as the gas bubbles through the liquid media, a portion of the dissolved gas is encapsulated within the internal aqueous environment of the liposomes. To enhance the dissolving of the gas into the liquid, it is desirable to promote mixing of the gas and the liquid, and bubbling the gas through the liquid assists in this. In the preferred embodiment, this mixing is further enhanced by providing the vessel with a convex shaped bottom (2) projecting into the vessel. The lower end of the tube discharges the gas near the most inward point (5) on the convex shaped bottom.

After the gas has been introduced into the vessel (1), the vessel is depressurized by ejecting the liquid therefrom. Ejection is accomplished by actuating a discharge lever (12), in the cap (10). Actuation of the discharge lever opens an outlet port (7) so that the gas pressure forces the liquid to enter the tube (3) at its lower end (4), flow up the tube and out of the vessel through the discharge port. Forcing the liquid through the tube promotes further mixing of the gas and liquid. Upon depressurization, the dissolved gas encapsulated by the liposomes comes out of solution and forms bubbles within the liposomes, thereby forming liposomes having encapsulated therein a gas.

Alternatively, the method described above could be practiced using the apparatus shown in FIG. 5. If desired, the liposomes may be pre-sized by injecting them from a syringe (33) through one or more filter(s) (30), through inlet/outlet port (35) and valve (39), and then through tube (38) into vessel (34). Alternatively, the liposomes are simply placed in a vessel (34). Vessel (34) is equipped with valves (39), inlet/outlet port (35), inlet/outlet port (36) and tube (38). The vessel (34) is constructed so that it can be pressurized with a gas or combination of gases such as carbon dioxide, oxygen, nitrogen, xenon, argon, neon and helium by means of a valve or inlet port (36) and external pressure source (37) which can be a gas line, tank or disposable cartridge. The valve(s) (39) may be constructed so as to be able to vent excess pressure without dispensing the liposomes. The vessel may be constructed of any suitable material, such as glass or acrylic, and may be disposable, if desired.

In use, the vessel (34) is first loaded with a liposomal containing solution, using if desired, syringe (33), with or without filter (30). The vessel is then pressurized with gas using external pressure source (37) which passes gas through inlet port (36) through valve (39) and tube (38) into vessel (34). Under pressure, the gas goes into solution and passes across the liposome membranes. When the pressure is released, gas bubbles form within the liposomes. The pressurized vessel (34) has an inlet/outlet port (35) to which one or more filters (30) may be attached. In FIG. 5, the use of Luer lock fittings (31) and (32) is illustrated as an example of a means for connecting the pressure vessel (34), filters (30) and syringe (33). However, any suitable means of coupling the devices may be employed. The pore size of suitable filters may vary widely between about 0.015 micron and about 10 microns. More than one filter, if desired, may be employed in serial connection. The function of the filter(s) (30) is threefold: to promote decavitation of any bubbles formed external to the liposomes after preparation of the gas-encapsulating liposomes; to promote sizing of the liposomes either before or after gas-encapsulation; and to remove non-liposomal solids from the suspension. The filter(s) (30) may in turn be connected to a syringe (33). When the vessel is filled with liposomes, they may be directed from the syringe (33) through the filter(s) (30) and through the inlet/outlet port (35) and valve (39) into pressure vessel (34). In addition, when the contents of vessel (34) are released by means of the outlet valve (35) of the vessel, the output stream may be directed through the filters (30) into the syringe (33). If desired, the vessel (34) may be directly loaded and unloaded without passing through inlet/outlet port (35) and valve (39), filter (30) and/or syringe (33). The advantage of this procedure is that the device can be pre-packaged as a stand-alone, sterile unit ready for use. It should also be noted that it is not necessary that either the filters or syringe be used as described, e.g., the output stream of the device may be directed into a separate container prior to being taken up, for example, into a syringe for injection.

Figure 6:
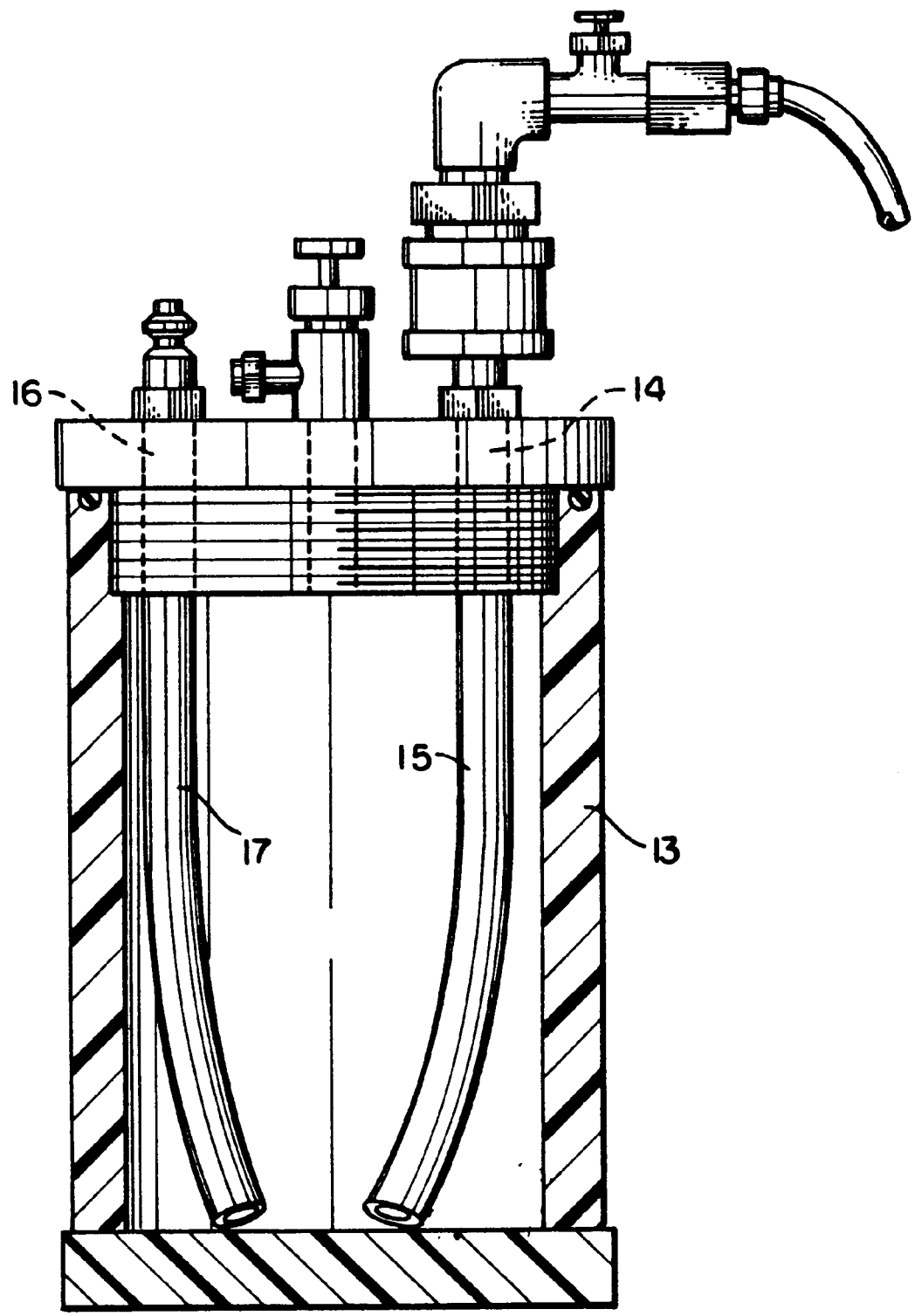
FIG. 6. This figure illustrates a further apparatus of the invention for synthesizing liposomes having encapsulated therein a gas. The gas enters a vessel in which a liquid media containing liposomes has been placed through an inlet port, flows through a tube and discharges into the bottom of the vessel. From the bottom of the vessel, the gas bubbles upward through the liquid. Depressurization is accomplished by opening a valve on a separate outlet port, thereby ejecting the liquid from the bottom of the vessel through the tube.

The method discussed above could also be practiced using the apparatus shown in FIG. 6, wherein the gas enters vessel (13) in which a liquid media containing liposomes has been placed, through inlet port (14), flows through tube (15) and discharges into the bottom of the vessel. The vessel may be constructed of any suitable material, such as glass or acrylic, and may be disposable, if desired. From the bottom of the vessel, the gas bubbles upward through the liquid. Depressurization is accomplished by opening a valve, not shown, on the outlet port (16), thereby ejecting the liquid from the bottom of the vessel through tube (17).

Figure 7:
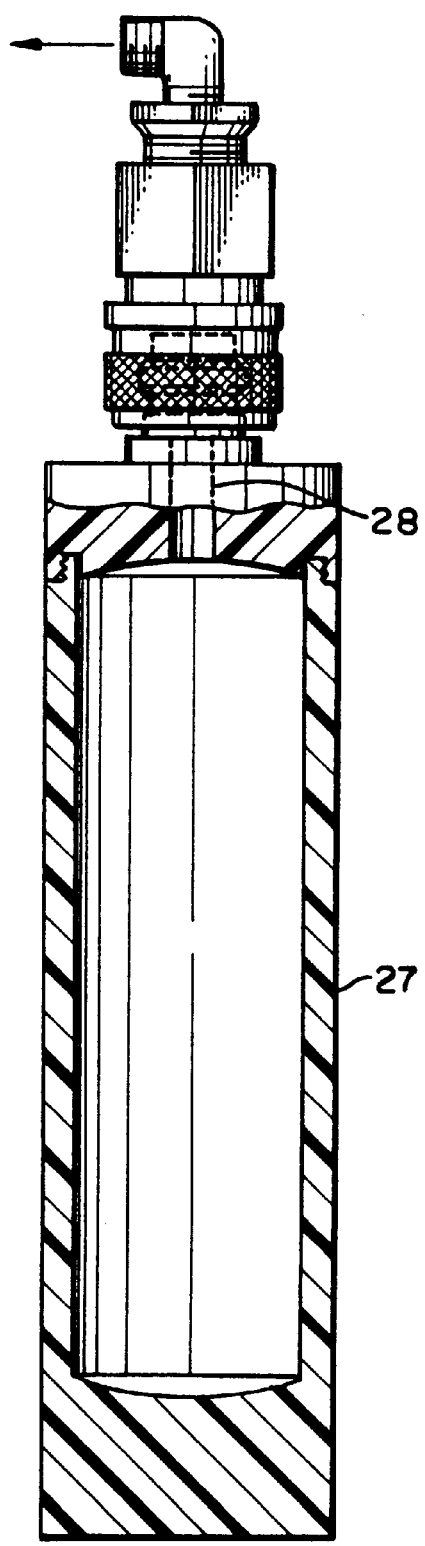
FIG. 7. This figure illustrates another apparatus for synthesizing liposomes having encapsulated therein a gas. As this figure illustrates, the apparatus required to practice the method of the invention need only be a simple vessel with a port for introducing and discharging the pressurized gas and liposomes.

Referring to FIG. 7, the apparatus required to practice such a method need only be a simple vessel (27) with a port (28) for introducing the liposomes and the pressurized gas and discharging the same. The vessel may be constructed of any suitable material, such as glass or acrylic, and may be disposable, if desired.

The inventors have discovered that with some gases, such as with carbon dioxide, it is helpful to bubble the gas through the liquid in order to dissolve the gas. Also, with some gases, such as with nitrogen, it is helpful to cool the liquid to approximately the 1–4° C. range. In carrying out the pressurization, pressures between about 2 and about 400 psi, preferably between about 30 and about 100 psi should be employed. The inventors have also discovered that it is preferable that the depressurization occur quickly over several seconds or less.

It should be noted that the method described above is particularly adapted for use with liposomes having membranes which are relatively permeable to the gas. However, the inventors have found that by subjecting the liposome-containing liquid media to high frequency sound waves, as discussed below, even relatively impermeable membrane compositions can be easily utilized. As a general rule and as noted above, membranes composed of significant amounts of sterols or composed largely of saturated lipids are relatively impermeable to certain gases such as carbon dioxide, however, egg phosphatidyl choline, for example, is highly permeable.

Figure 8:
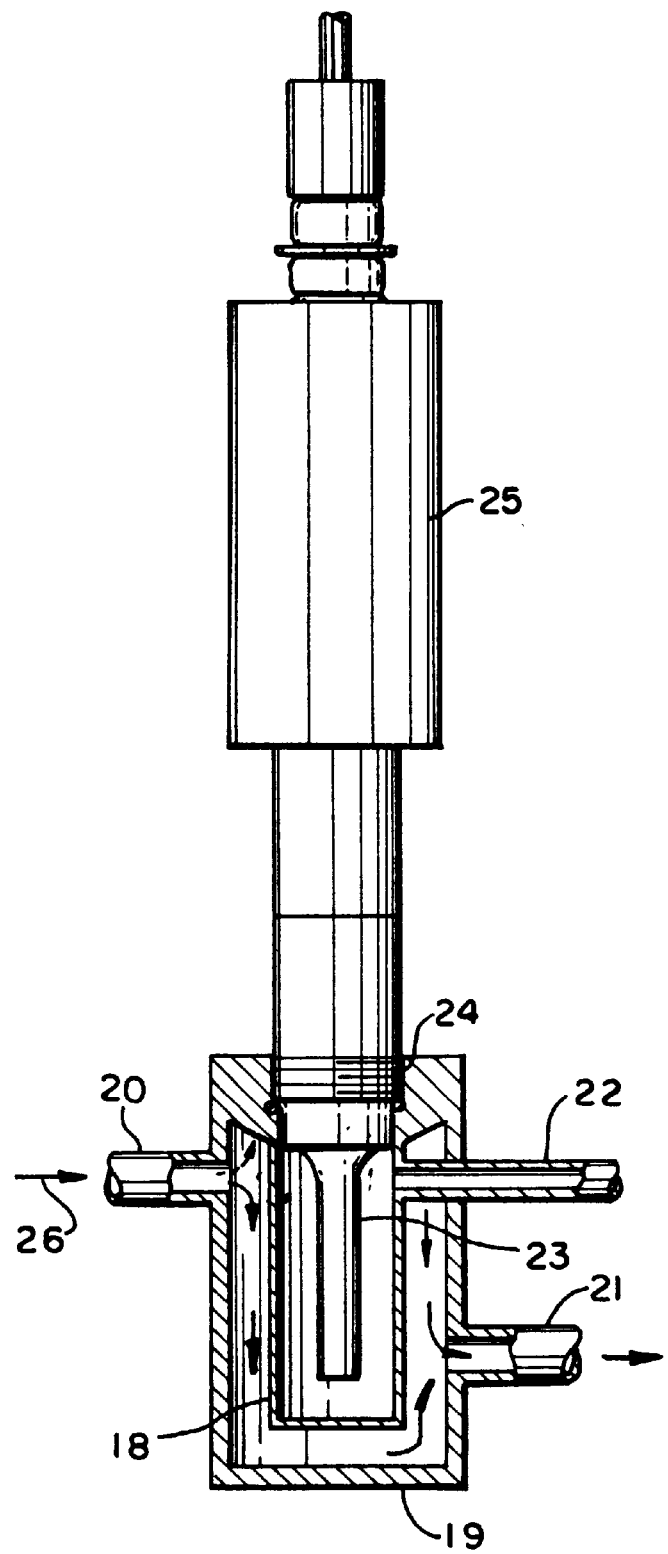
FIG. 8. This figure illustrates another apparatus for synthesizing liposomes having encapsulated therein a gas. This apparatus is utilized by placing a liquid media which contains liposomes in a vessel jacketed by a chamber through which a coolant circulates. A high frequency sound wave generator is attached to the vessel. In use, the vessel is pressurized using a gas introduced through a gas port. The sound wave generator transforms electrical energy into mechanical oscillations and transmits the oscillations into the liquid through a horn which extends into the vessel. As the liposomes break up and reform as a result of the mechanical forces, they encapsulate the dissolved gas within their internal aqueous core. Following sonication, the vessel is depressurized and the encapsulated gas forms bubbles, thereby transforming the liposomes into gas-containing liposomes.

There is shown in FIG. 8 an apparatus for synthesizing liposomes containing gas which uses sonication. The apparatus is utilized by placing a liquid media containing liposomes, in a vessel (18). A high frequency sound wave generator (25), which may be a Sonicator (cr), available from Heat Systems-Ultrasonics, Inc., is attached to the vessel using mating threads (24) formed in the inlet to the vessel and the outside of the generator. The vessel is then pressurized using a gas introduced through gas port (22). In the preferred embodiment, the vessel is pressurized to between about 30 and about 120 psi using a gas, such as carbon dioxide, cooled into approximately the 1–4° C. range, thereby promoting the dissolving of the gas into the liquid media. The vessel is jacketed by a chamber (19), through which a liquid or gaseous coolant (26) circulates via inlet and outlet ports (20), (21) respectively, so as to maintain the temperature of the liquid preferably between about 1° C. and about 4° C. range during the sonication process described below.

The sound wave generator (25) transforms electrical energy into mechanical energy, at a frequency of approximately 20 kHz and an amplitude approximately in the range of 30–120 $\mu$m, by oscillating piezoelectric crystals. These oscillations are transmitted and focused into the liquid through a horn (23) which extends into the vessel (18), causing high frequency sound waves to propagate through the liquid. The sound waves cause cavitation in the liquid, i.e., the high frequency formation and collapse of microscopic bubbles. The process of inducing cavitation by high frequency sound waves is referred to as sonication. The cavitation induces a shearing and tearing action in the liquid, causing the large multilamellar liposomes to tear and reform into smaller oligolamellar liposomes and eventually, depending on the duration and intensity of the sonication, unilamellar liposomes. As the liposomes break up and reform, they encapsulate the dissolved gas within their internal aqueous cores.

Following sonication, the vessel is depressurized and the encapsulated gas forms bubbles, thereby transforming the liposomes into gas containing liposomes as before. However, since the gas was introduced into the liposomes during their break-up caused by the sonication, liposomes having relatively impermeable membranes can be used. By using such membranes, an added advantage in stability is achieved, that is, the gas bubbles do not diffuse back across the membrane as readily as with other methods and membranes. Thus, the sonication process allows the formation of more stable gas containing liposomes. The inventors have found that generally cholesterol-based liposomal membranes are relatively impermeable.

Other techniques in addition to sonication can be used to synthesize liposomes having encapsulated therein a gas, including microemulsification, extrusion, microfluidization, homogenization and the like, the requirement being that the synthetic process be conducted under pressurization, preferably at low temperatures.

In each of the foregoing methods for preparing gas-containing liposomes, the liposome preparation is preferably stored under pressure with the gas in solution or the gas pressurization and depressurization process is carried out at or about the time of use.

The liposomes of the present invention and those produced by the apparatus and method of the invention are useful in imaging a patient using ultrasound. The present invention is useful in imaging a patient generally, and/or in specifically diagnosing the presence of diseased tissue in a patient. The patient can be any type of mammal, but most preferably is a human. The method of the invention is particularly useful in diagnosing the vasculature, that is, the arterial system, the venous system and the heart. It is also particularly useful in providing images of the patient's liver, spleen or kidney.

The imaging process of the present invention may be carried out by administering a liposome of the invention, that is a liposome selected from the group consisting of an ionophore-containing liposome having encapsulated therein a pH-activated gaseous precursor, a liposome having encapsulated therein a photo-activated gaseous precursor, a liposome having encapsulated therein a temperature-activated gaseous precursor, and/or a liposome having encapsulated therein a solid or liquid contrast enhancing agent, to a patient, and then scanning the patient using ultrasound imaging to obtain physical images of an internal region of a patient and/or of any diseased tissue in that region. By region of a patient, it is meant the whole patient or a particular area or portion of the patient.

Any of the various types of ultrasound imaging devices can be employed in the practice of the invention, the particular type or model of the device not being critical to the method of the invention.

For intravascular use the contrast agent is generally injected intravenously, but may be injected intra-arterially also. As injections are performed, ultrasonic images are obtained with an ultrasound scanner. In the case of intravascular injection, the liposomal contrast agents generally have a mean outer diameter of smaller than about 2 to about 3 microns (small enough to pass through the pulmonary circulation). In other non-vascular applications, the liposomal contrast agent may be injected directly into the area to be scanned, into sites such as sinus tracts or the uterine cavity, for example, to assess patency of the fallopian tubes. In cases of non-vascular injection, the liposomal contrast agent diameter is not constrained by the necessity of passing through the pulmonary microvasculature. Therefore larger liposomes can be used to maximize echogenicity.

In administering the liposomes of the present invention, dosage is typically initiated at lower levels and increased until the desired contrast enhancement in the patient is achieved. In carrying out the method of the invention, the liposomes can be used alone, in combination with one another, or in combination with other diagnostic and/or therapeutic agents. Preferable routes of administration will be readily apparent to those skilled in the art. As those skilled in the art will recognize, such parameters as dosage and preferable administration routes will vary depending upon the age, weight and mammal to be diagnosed, the particular type of liposome to be employed, and most importantly, the particular area of the patient to be scanned.

The following Examples are merely illustrative of the present invention and should not be considered as limiting the scope of the invention in any way. These examples and equivalents thereof will become more apparent to those versed in the art in light of the present disclosure, and the accompanying Claims.

EXAMPLES

Example 1

Egg phosphatidylcholine, 1 gram, was suspended in 100 cc of physiological saline at room temperature to form a dispersion of multilamellar liposome vesicles. The liposomes were then placed in the vessel of FIG. 5. The outlet valve on the vessel was then sealed and the system was pressurized with between 30 to 50 psi $CO_2$ gas. The suspension is then emptied into a flask and the non-encapsulated $CO_2$ gas was allowed to escape. $CO_2$ gas entrapped within the vesicles remained entrapped. The gas filled vesicles surprisingly did not float, but were distributed evenly in solution. The resultant gas filled liposomes were found to be intensely echogenic on ultrasound.

Example 2

Vesicles were also formed as described in Example 1, except that vesicle formation was carried out in the presence of bicarbonate and the ionophore A23187 resulting in bicarbonate encapsulated liposomes contacting that ionophore. Acid was added to the external aqueous phase in order to lower the pH within the vesicles. The bicarbonate entrapped within the vesicles was found to form $CO_2$ gas and water.

Examples 3–18

A. Liposome Preparation

To prepare multilamellar vesicles (MLV's) pure egg phosphatidylcholine (EPC) obtained from Avanti Polar Lipids (Birmingham, Ala.) was suspended in phosphate buffered saline (PBS) and swirled by hand. In other cases vesicles of defined size were prepared by a process of extrusion with or without a preceding freeze-thaw process. Two different lipid mixtures were tested, either pure EPC or a mixture of 80 mole percent EPC with 20 mole percent cholesterol. Typically, for the EPC/cholesterol vesicles 3.6 mmol (2.83 g) of EPC and 1.2 mmol (0.48 g) of cholesterol were dissolved together, in a minimum volume of chloroform, in a 250-ml round-bottom flask. The chloroform was removed by rotary evaporation under reduced pressure to leave a thin film on the walls of the flask; the contents were then held under reduced pressure (less than 0.1 mm Hg) for at least 2 hours to remove residual solvent. For mixtures of pure. EPC the step of suspension in chloroform was omitted. For both pure EPC and the dried film of EPC/cholesterol, the lipid was dispersed by vigorous mixing in 20 cc of neutral pH phosphate buffered saline (PBS).

Vesicles prepared both with and without freeze-thaw were synthesized. For vesicles subjected to freeze-thaw the multilamellar vesicles formed upon dispersion were transferred to cryovials and then quench frozen in liquid nitrogen. The cryovials were then placed in warm water until the lipid suspension had completely thawed. This cycle of freezing and thawing was repeated four more times. Both the vesicles subjected to freeze-thaw and those which were not freeze-thawed were then sized by ten passes under nitrogen pressure (approx. 100 psi) through two stacked 2 micron filters (Nucleopore, Pleasanton, Calif.) using the extruder device (Lipex Biomembranes, Vancouver, British Columbia, Canada). A portion of this sized preparation was then passed ten times through two stacked 0.4 micron filters, a portion of this was then passed ten additional times through 0.2 micron filters, and finally a portion of this was passed ten times through 0.030 micron filters. The above was conducted for the EPC/cholesterol vesicles but filter sizes of only 0.4 and 0.2 microns were tested for the vesicles composed of pure EPC. The sizes of the resultant vesicles were determined by quasi elastic light scattering with a Nicomp (Goleta, Calif.) Model 270 particle sizer operating at 634.2 nm by standard cumulants analysis.

B. Pressurization

Pressurization of the liposome solutions and controls of PBS was accomplished with a soda seltzer bottle using carbon dioxide cartridges (FIG. 4). In all experiments for dilution of liposomes and as controls only degassed solutions of PBS were used. All liquids were degassed immediately prior to use. Degassification of solutions was accomplished by reducing pressure under vacuum. In pressurization of all solutions 50 cc of liquid was poured into the seltzer bottle and the system then sealed. Pressurization was then accomplished by engaging the $CO_2$ cartridge with the bottle. After 1 minute the pressure was released from the bottle and the solution poured from the bottle. The seltzer bottle was equipped with a pressure gauge and the pressure was measured during each experiment. Solutions which were exposed to gassification included various dilutions of the different sizes of liposomes and pure PBS.

C. Ultrasound Imaging

Ultrasound Imaging was performed with an Acuson 128 scanner (Milpitas, Calif.) using a 7.5 megahertz linear array transducer. Post-processing function was linear with pre-processing set at 0 and persistence at 2. Phantom solutions (controls and liposomal agents) at variable concentrations and constant volumes and depth were scanned at 30 to 60 dB gain settings within thin plastic containers. Multifocal zones with a decreased frame rate were used for most images. For quantitative measurements a 1 cm circle was positioned on the images at a position 2 cm below the transducer and the number of reflections within the circle was counted. At the time of measurement of acoustic reflections the ultrasonographer was blinded to information as to which contrast agent or control was being studied.

D. Results

The sizes of the resulting vesicles and their echogenicity on ultrasound are shown in Tables I and II. The size of the vesicles is controlled by the filters used in the extrusion process. For the MLV's prepared without extrusion the size range is quite variable. For those vesicles which underwent the extrusion process the size range is comparatively narrow.

In the ultrasound imaging experiments of the phantoms containing the different contrast agents large reflections were seen at 30 dB for the first minute or two after the ultrasound contrast agents were pressurized and then poured into the plastic phantom dishes. These large reflections decayed quickly however and were not visible after several minutes. The reflections which persisted after the first 2 to 3 minutes were of much finer size and more regular in appearance.

The number of reflections counted within a 1 cm diameter circle over time for the different solutions is shown in Tables I and II. The 0.4 micron vesicles composed of pure EPC synthesized by extrusion but without freeze-thaw had the greatest echogenicity after exposure to pressurization and echogenicity was sustained for 2 hours after the pressurization process. By comparison the phantom containing a similar concentration of the same vesicles without exposure to pressurization had no internal echoes at all at 30 minutes after they were poured into the phantom. MLV's synthesized of pure EPC had the next highest echogenicity. All of the vesicles which contained cholesterol had lower echogenicity than the vesicles composed of pure EPC. The control solution of PBS exposed to pressurization but not containing liposomes had echoes during the first minute or two but these echoes decayed rapidly to zero after several minutes (Table II).

The greatest echogenicity was seen in 0.4 micron vesicles composed of pure EPC which were extruded but not freeze-thawed. Vesicles of the same size which were freeze-thawed had less echogenicity. Vesicles of this size subjected to freeze-thaw will be unilamellar whereas those not subjected to freeze-thaw of this size will be oligolamellar.

TABLE I

Number of Reflections at 60 dB

| Example | | Time in minutes | | | | | | |
|---|---|---|---|---|---|---|---|---|
| | | 5 | 10 | 20 | 30 | 45 | 60 | 120 |
| 3 | (0.4μ, no FT) | — | — | — | 95 | 89 | 116 | 109 |
| 4 | (0.4μ + FT) | — | — | — | 52 | 69 | — | — |
| 5 | (0.2μ + FT) | — | — | — | 26 | 52 | — | — |
| 6 | (MLV's) | — | — | 58 | 72 | — | — | — |
| 7 | (Ex. 6 at 94 psi) | — | 60 | 69 | — | — | — | — |
| 8 | (MLV's, no gas) | 84 | 32 | 10 | — | — | — | — |
| 9 | (Ex. 3, no gas) | 18 | — | — | 0 | — | — | — |
| 10 | (PBS) | 0 | — | — | — | — | — | — |
| 11 | (PBS + gas) | 12 | 10 | 3 | — | — | — | — |

*Data above from counting number of reflections within 1 cm diameter circle positioned 2 cm from transducer on images obtained by scanning 400 cc solutions of ultrasound contrast agents with 7.5 mHz linear array transducer. The liposomes in Examples 3 through 6 were pressurized with 52 to 54 psi $CO_2$ gas. The liposomes in Examples 3, 4 and 5 were extruded 10 times through filters as specified, in Examples 4 and 5, these liposomes were then exposed to 5 cycles of freeze-thaw, and in Example 3, these liposomes were not freeze-thawed. The liposomes in Example 6 involved multilamellar vesicles (MLV's) prepared by simple mixing of egg phosphatidylcholine (EPC). The liposomes in Example 7 were exposed to higher pressure of 94 psi. The liposomes in Example 8 and 9 are control samples of vesicles, with those in Example 8 involving MLV's and those in Example 9 being 0.4μ vesicles (no freeze-thaw) without exposure to gas. In Example 10, the sample is phosphate buffered normal saline (PBS) without exposure to gas. In all vesicle preparations final lipid concentration is 1.25 micromoles/ml. The notation (–) indicates that the number of reflections was not measured.

TABLE II

Number of Reflections at 60 dB

| Example | | Time in minutes | | | | | | |
|---|---|---|---|---|---|---|---|---|
| | | 1 | 2 | 3 | 10 | 15 | 20 | 30 |
| 12 | (0.2μ) | 22 | 30 | 33 | — | — | — | 27 |
| 13 | (MLV's) | 40 | 27 | 34 | — | — | — | 48 |
| 14 | (2.0μ EPC/Chol.) | — | 18 | — | — | 15 | 15 | — |
| 15 | (MLV's 50 nm EPC/Chol.) | 12 | 23 | 13 | — | — | 16 | 15 |
| 16 | (0.4μ EPC/Chol.) | 15 | 22 | — | — | 11 | — | 15 |
| 17 | (PBS + gas) | 15 | 7 | 6 | 10 | 3 | 0 | 0 |
| 18 | (PBS, no gas) | 23 | 25 | 4 | — | — | 0 | — |

*Lipid concentration in the above is 0.225 micromoles of lipid per ml. The liposomes in Examples 12 and 13 are pure EPC, the liposomes in Example 13 are MLV's as in Table I, and the liposomes in Example 12 are a dilute version of those employed in Example 5 from Table I. Examples 12, 14, 15 and 16 were produced by extrusion through filter pore sizes as specified and Examples 14, 15 and 16 contain 80% EPC/20% Cholesterol.

Having described the invention above, it will be obvious to one skilled in the art that various parameters such as liposome size and membrane composition are selected to achieve the desired effect in terms of biodistribution and imaging.

Various modifications of the invention in addition to those shown and described herein will be apparent to those skilled in the art from the foregoing description. Such modifications are also intended to fall within the scope of the appended claims.

What is claimed is:

1. A method of providing an image of an internal region of a patient comprising:
   (a) providing a vessel containing a solution which comprises lipid vesicles and a gaseous precursor;
   (b) depressurizing said vessel to form gas bubbles within said lipid vesicles;
   (c) administering to the patient said gas encapsulated lipid vesicles; and
   (d) scanning the patient using ultrasound imaging to obtain visible images of the region.

2. A method according to claim 1 wherein said lipid vesicles comprise one or more lipids selected from the group consisting of phosphatidylcholine, phosphatidylethanolamine and phosphatidic acid.

3. A method according to claim 1 wherein said lipid vesicles further comprise a polymer on the surface of said vesicles.

4. A method according to claim 3 wherein said polymer comprises polyethyleneglycol.

5. A method according to claim 2 wherein said lipid vesicles further comprise a polymer on the surface of said vesicles.

6. A method according to claim 5 wherein said polymer comprises polyethyleneglycol.

7. A method according to claim 1 wherein said lipid vesicles comprise liposomes.

8. A method according to claim 7 wherein said liposomes are selected from the group consisting of unilamellar liposomes, oligolamellar liposomes and multilamellar liposomes.

9. A method according to claim 8 wherein said liposomes comprise unilamellar liposomes.

10. A method according to claim 9 wherein said liposomes comprise one or more phospholipids.

11. A method according to claim 9 wherein said lipid is selected from the group consisting of cholesterol, phosphatidylcholine, phosphatidylethanolamine, phosphatidylserine, phosphatidylglycerol, phosphatidic acid, phosphatidylinositol, lysolipids, fatty acids, sphingomyelin, glycosphingolipids, glucolipids, glycolipids, sulphatides, lipids with ether and ester-linked fatty acids and polymerizable lipids.

12. A method according to claim 11 wherein said lipid is a polymerizable lipid.

13. A method according to claim 11 wherein said liposomes further comprise polyethyleneglycol.

14. A method according to claim 8 wherein said liposomes are selected from the group consisting of oligolamellar liposomes and multilamellar liposomes.

15. A method according to claim 14 wherein said liposomes comprise one or more phospholipids.

16. A method according to claim 14 wherein said lipid is selected from the group consisting of cholesterol, phosphatidylcholine, phosphatidylethanolamine, phosphatidylserine, phosphatidylglycerol, phosphatidic acid, phosphatidylinositol, lysolipids, fatty acids, sphingomyelin, glycosphingolipids, glucolipids, glycolipids, sulphatides, lipids with ether and ester-linked fatty acids and polymerizable lipids.

17. A method according to claim 16 wherein said lipid is a polymerizable lipid.

18. A method according to claim 16 wherein said liposomes further comprise polyethyleneglycol.

19. A method according to claim 1 wherein said lipid in said vesicles is selected from one or more phospholipids.

20. A method according to claim 1 wherein said lipid is selected from the group consisting of cholesterol, phosphatidylcholine, phosphatidylethanolamine, phosphatidylserine, phosphatidylglycerol, phosphatidic acid, phosphatidylinositol, lysolipids, fatty acids, sphingomyelin, glycosphingolipids, glucolipids, glycolipids, sulphatides, lipids with ether and ester-linked fatty acids and polymerizable lipids.

21. A method according to claim 20 wherein said lipid is a polymerizable lipid.

22. A method according to claim 20 wherein said lipid further comprises polyethyleneglycol.

23. A method for diagnosing the presence of diseased tissue in a patient comprising:
(a) providing a vessel containing a solution which comprises lipid vesicles and a gaseous precursor;
(b) depressurizing said vessel to form gas bubbles within said lipid vesicles;
(c) administering to the patient said gas encapsulated lipid vesicles; and
(d) scanning the patient using ultrasound imaging to obtain visible images of any diseased tissue in the patient.

24. A method according to claim 23 wherein said lipid vesicles comprise one or more lipids selected from the group consisting of phosphatidylcholine, phosphatidylethanolamine and phosphatidic acid.

25. A method according to claim 23 wherein said lipid vesicles further comprise a polymer on the surface of said vesicles.

26. A method according to claim 25 wherein said polymer comprises polyethyleneglycol.

27. A method according to claim 24 wherein said lipid vesicles further comprise a polymer on the surface of said vesicles.

28. A method according to claim 27 wherein said polymer comprises polyethyleneglycol.

29. A method according to claim 23 wherein said lipid vesicles comprise liposomes.

30. A method according to claim 29 wherein said liposomes are selected from the group consisting of unilamellar liposomes, oligolamellar liposomes and multilamellar liposomes.

31. A method according to claim 30 wherein said liposomes comprise unilamellar liposomes.

32. A method according to claim 31 wherein said liposomes comprise one or more phospholipids.

33. A method according to claim 31 wherein said lipid is selected from the group consisting of cholesterol, phosphatidylcholine, phosphatidylethanolamine, phosphatidylserine, phosphatidylglycerol, phosphatidic acid, phosphatidylinositol, lysolipids, fatty acids, sphingomyelin, glycosphingolipids, glucolipids, glycolipids, sulphatides, lipids with ether and ester-linked fatty acids and polymerizable lipids.

34. A method according to claim 33 wherein said lipid is a polymerizable lipid.

35. A method according to claim 33 wherein said liposomes further comprise polyethyleneglycol.

36. A method according to claim 30 wherein said liposomes are selected from the group consisting of oligolamellar liposomes and mutltilamellar liposomes.

37. A method according to claim 36 wherein said liposomes comprise one or more phospholipids.

38. A method according to claim 36 wherein said lipid is selected from the group consisting of cholesterol, phosphatidylcholine, phosphatidylethanolamine, phosphatidylserine, phosphatidylglycerol, phosphatidic acid, phosphatidylinositol, lysolipids, fatty acids, sphingomyelin, glycosphingolipids, glucolipids, glycolipids, sulphatides, lipids with ether and ester-linked fatty acids and polymerizable lipids.

39. A method according to claim 38 wherein said lipid is a polymerizable lipid.

40. A method according to claim 38 wherein said liposomes further comprise polyethyleneglycol.

41. A method according to claim 23 wherein said lipid in said vesicles is selected from one or more phospholipids.

42. A method according to claim 23 wherein said lipid is selected from the group consisting of cholesterol, phosphatidylcholine, phosphatidylethanolamine, phosphatidylserine, phosphatidylglycerol, phosphatidic acid, phosphatidylinositol, lysolipids, fatty acids, sphingomyelin, glycosphingolipids, glucolipids, glycolipids, sulphatides, lipids with ether and ester-linked fatty acids and polymerizable lipids.

43. A method according to claim 42 wherein said lipid is a polymerizable lipid.

44. A method according to claim 42 wherein said lipid further comprises polyethyleneglycol.

45. A method for the preparation of a lipid vesicle having encapsulated therein a gas comprising:
(a) providing a vessel containing a solution which comprises lipid vesicles and a gaseous precursor; and
(b) depressurizing said vessel to form gas bubbles within said lipid vesicles.

46. A method according to claim 45 which comprises one or more lipids selected from the group consisting of phosphatidylcholine, phosphatidylethanolamine and phosphatidic acid.

47. A method according to claim 46 wherein said lipid vesicle further comprises a polymer on the surface of said vesicle.

48. A method according to claim 47 wherein said polymer comprises polyethyleneglycol.

49. A method according to claim 45 wherein said lipid vesicle further comprises a polymer on the surface of said vesicle.

50. A method according to claim 49 wherein said polymer comprises polyethyleneglycol.

51. A method according to claim 45 wherein said lipid vesicle comprises liposomes.

52. A method according to claim 51 wherein said liposomes are selected from the group consisting of unilamellar liposomes, oligolamellar liposomes and multilamellar liposomes.

53. A method according to claim 52 wherein said liposomes comprise unilamellar liposomes.

54. A method according to claim 53 wherein said liposomes comprise one or more phospholipids.

55. A method according to claim 53 wherein said lipid is selected from the group consisting of cholesterol, phosphatidylcholine, phosphatidylethanolamine, phosphatidylserine, phosphatidylglycerol, phosphatidic acid, phosphatidylinositol, lysolipids, fatty acids, sphingomyelin, glycosphingolipids, glucolipids, glycolipids, sulphatides, lipids with ether and ester-linked fatty acids and polymerizable lipids.

56. A method according to claim 55 wherein said lipid is a polymerizable lipid.

57. A method according to claim 55 wherein said liposomes further comprise polyethyleneglycol.

58. A method according to claim 52 wherein said liposomes are selected from the group consisting of oligolamellar liposomes and multilamellar liposomes.

59. A method according to claim 58 wherein said liposomes comprise one or more phospholipids.

60. A method according to claim 58 wherein said lipid is selected from the group consisting of cholesterol, phosphatidylcholine, phosphatidylethanolamine, phosphatidylserine, phosphatidylglycerol, phosphatidic acid, phosphatidylinositol, lysolipids, fatty acids, sphingomyelin, glycosphingolipids, glucolipids, glycolipids, sulphatides, lipids with ether and ester-linked fatty acids and polymerizable lipids.

61. A method according to claim 60 wherein said lipid is a polymerizable lipid.

62. A method according to claim 60 wherein said liposomes further comprise polyethyleneglycol.

63. A method according to claim 45 wherein said lipid in said vesicle is selected from one or more phospholipids.

64. A method according to claim 45 wherein said lipid is selected from the group consisting of cholesterol, phosphatidylcholine, phosphatidylethanolamine, phosphatidylserine, phosphatidylglycerol, phosphatidic acid, phosphatidylinositol, lysolipids, fatty acids, sphingomyelin, glycosphingolipids, glucolipids, glycolipids, sulphatides, lipids with ether and ester-linked fatty acids and polymerizable lipids.

65. A method according to claim 64 wherein said lipid is a polymerizable lipid.

66. A method according to claim 45 wherein said vesicle further comprises polyethyleneglycol.

67. A method according to claim 1 wherein said solution contained in said vessel is solvent-free.

68. A method according to claim 23 wherein said solution contained in said vessel is solvent-free.

69. A method according to claim 45 wherein said solution contained in said vessel is solvent-free.

* * * * *

UNITED STATES PATENT AND TRADEMARK OFFICE
CERTIFICATE OF CORRECTION

PATENT NO. : 5,985,246
DATED : November 16, 1999
INVENTOR(S) : Evan C. Unger

It is certified that error appears in the above-identified patent and that said Letters Patent is hereby corrected as shown below:

Title page,
Column 2,
Under OTHER PUBLICATIONS, at Villanueva et al., please delete "Patters" and insert -- Patterns -- therefor.
At Keller et al., second line thereof, please delete "Microcirulation" and insert -- Microcirculation -- therefor.

Page 2,
Under U.S. PATENT DOCUMENTS, first column, at 4,569,836, please insert, after Gordon, "....................424/1.1".

Page 3,
Under FOREIGN PATENT DOCUMENTS, second column, please delete "WO 90/09152" and insert -- WO 90/01952 -- therefor.

Page 4,
Under OTHER PUBLICATIONS, first column, at Feinstein et al., third line thereof, please delete "*JAAC*" and insert -- *JACC* -- therefor.
Under OTHER PUBLICATIONS, second column, at Fukuda et al., second line thereof, plase delete "Diotadecyldimethylammonium" and insert -- Dioctadecyldimethylammonium -- therefor.
Under OTHER PUBLICATIONS, second column, at Shiina et al., please delete "Hyperthermiaby" and insert -- Hyperthermia by --

Page 5,
Under OTHER PUBLICATIONS, first column, at Felgner et al., please delete "lipid-mediate" and insert -- lipid-mediated -- therefor.
Under OTHER PUBLICATIONS, first column, at *Mammalian Cell Biotechnology: A Practical Approach*, second line thereof, plase delete "199" and insert -- 1991 -- therefor.
Under OTHER PUBLICATIONS, first column, at Poznansky et al., please delete "Biologica" and insert -- Biological -- therefor.
Under OTHER PUBLICATIONS, second column, ate Santaella et al., second line thereof, please delete "Lipsomes" and insert -- Liposomes -- therefor.
Under OTHER PUBLICATIONS, second column, please delete "Ter-Pogossia *Tomography*, Kee, et al., n." and insert -- Ter-Pogossian, Lee et al., eds. -- therefor.
Under OTHER PUBLICATIONS, second column, at Ter-Pogossia, second line thereof, please delete "*Computed Body* eds." and insert -- *Computed Body Tomography* -- Therefor.
Under OTHER PUBLICATIONS, second column, at Aronberg, please delete "Kee" and

UNITED STATES PATENT AND TRADEMARK OFFICE
CERTIFICATE OF CORRECTION

PATENT NO. : 5,985,246
DATED : November 16, 1999
INVENTOR(S) : Evan C. Unger

It is certified that error appears in the above-identified patent and that said Letters Patent is hereby corrected as shown below:

Column 10,
Line 53, please delete "is FIG. 4" and insert -- in FIG. 4 -- therefor.

Signed and Sealed this

Thirtieth Day of October, 2001

*Attest:*

*Attesting Officer*

NICHOLAS P. GODICI
*Acting Director of the United States Patent and Trademark Office*